(12) United States Patent
Fiering et al.

(10) Patent No.: US 9,377,422 B2
(45) Date of Patent: Jun. 28, 2016

(54) SYSTEM AND METHOD FOR A MICROFLUIDIC CALORIMETER

(75) Inventors: Jason O. Fiering, Boston, MA (US); Dale Larson, Waban, MA (US); Gregory Kowalski, Beverly, MA (US); Mehmet Sen, Boston, MA (US)

(73) Assignees: The Charles Stark Draper Laboratory, Inc., Cambridge, MA (US); Northeastern University, Boston, MA (US)

( * ) Notice: Subject to any disclaimer, the term of this patent is extended or adjusted under 35 U.S.C. 154(b) by 305 days.

(21) Appl. No.: 13/350,022

(22) Filed: Jan. 13, 2012

(65) Prior Publication Data

US 2012/0264224 A1    Oct. 18, 2012

Related U.S. Application Data

(60) Provisional application No. 61/433,167, filed on Jan. 14, 2011.

(51) Int. Cl.
*G01N 25/48* (2006.01)
*G01N 25/00* (2006.01)
(Continued)

(52) U.S. Cl.
CPC ............. *G01N 25/482* (2013.01); *B82Y 15/00* (2013.01); *G01K 17/006* (2013.01); *G01N 21/05* (2013.01); *G01N 21/554* (2013.01); *G01N 25/4873* (2013.01); *G01N 2021/0346* (2013.01)

(58) Field of Classification Search
CPC . G01N 25/4846; G01N 25/48; G01N 25/482; G01N 25/4866; G01N 27/06; G01N 30/96; G01N 27/021; G01N 27/3271; G01N 2030/965; G01K 17/00

USPC ................................................. 436/147, 150
See application file for complete search history.

(56) References Cited

U.S. PATENT DOCUMENTS

2008/0014576 A1    1/2008   Jovanovich et al.
2008/0278728 A1    11/2008  Tetz et al.
(Continued)

FOREIGN PATENT DOCUMENTS

WO    WO-2012/097221 A1    7/2012

OTHER PUBLICATIONS

Calorimetric Biosensors with Integrated Microfluidic Channels Yuyan Zhang, Srinivas Tadigadapa Biosensors and Bioelectronics 19 (2004) 1733-1743.*

(Continued)

*Primary Examiner* — Krishnan S Menon
*Assistant Examiner* — Dwan A Gerido
(74) *Attorney, Agent, or Firm* — Edward A. Gordon; Foley & Lardner LLP

(57) ABSTRACT

Systems and methods are disclosed herein for a microfluidic calorimeter apparatus. A microfluidic calorimeter system includes a calorimetry apparatus and a processor in connection with the apparatus. The apparatus includes a microfluidic laminar flow channel connected to two inlets for flowing fluid into the laminar flow channel. Below the laminar flow channel is a plurality of microscale temperature sensors at known positions in the channel. The processor is in connection with the discrete temperature sensors and determines a calorimetry measurement based on local temperatures derived from data output by the microscale temperature sensors and the respective positions of the sensors in the channel.

30 Claims, 11 Drawing Sheets
(1 of 11 Drawing Sheet(s) Filed in Color)

(51) Int. Cl.
- *B82Y 15/00* (2011.01)
- *G01K 17/00* (2006.01)
- *G01N 21/05* (2006.01)
- *G01N 21/552* (2014.01)
- *G01N 21/03* (2006.01)

(56) References Cited

U.S. PATENT DOCUMENTS

| | | | |
|---|---|---|---|
| 2008/0285039 A1 | 11/2008 | Que et al. | |
| 2010/0120163 A1* | 5/2010 | Larson et al. | 436/147 |
| 2012/0264224 A1 | 10/2012 | Fiering et al. | |

OTHER PUBLICATIONS

Fast Temperature Sensing Using Changes in Extraordinary Optical Transmission through an Array of Subwavelength Apertures Gregory J. Kowalski, Amir Talakoub, Jin Ji, J. Garland O'Connel, Mehmet Sen, Dale Larson Optical Engineering 48(10), Oct. 2009.*

Thermal Management Design of a Nanoscale Biocalorimeter Gregory J. Kowalski, Amir Talakoub, Dale Larson Proceedings of IPACK, Jul. 8-12, 2007.*

Kowalski, G.J. et al. "Fast temperature sensing using changes in extraordinary optical transmission through an array of subwavelength apertures" Optical Engineering, vol. 48, No. 10, pp. 1-9, Oct. 2009.

Kowalski, G.J. et al. "Thermal management design of a nanoscale biocalorimeter" Proceedings of the ASME Interpack Conference 2007, vol. 2, pp. 939-946, 2007.

Yu, J. et al., "Nanoscale Calorimeter Development" The Young Scholars Program, Northeastern University, 2009.

International Search Report and Written Opinion of PCT/US2012/021198 dated Apr. 23, 2012.

Ji, J. et al. "High-throughput nanohhole array based system to monitor multiple binding events in real time," Analytical Chemistry, vol. 80, pp. 2491-2498, 2008.

Krishnan, A. et al. "Evanescently coupled resonance in surface plasmon enhanced transmission," Optics Communications, vol. 200, pp. 1-7, 2001.

Leach, A. et al. "Flow injection analysis in a microfluidic format," Analytical Chemistry, vol. 75, No. 5, pp. 967-972, 2003.

Lindquist, N. et al. "Sub-micron resolution surface plasmon resonance imaging enabled by nanohole arrays with surrounding Bragg mirrors for enhanced sensitivity and isolation," Lab on a Chip, vol. 9, pp. 382-387, 2009.

Pradere, C. et al. "Processing of temperature field in chemical microreactors with infrared thermography," QIRT, vol. 3, No. 1, pp. 117-135, 2006.

US Office Action in U.S. Appl. No. 14/211,486 DTD May 22, 2015.

International Preliminary Report on Patentability mailed Sep. 24, 2015 in PCT App No. PCT/US2014/027437.

US Office Action in U.S. Appl. No. 14/211,486 dated Sep. 15, 2015.

\* cited by examiner

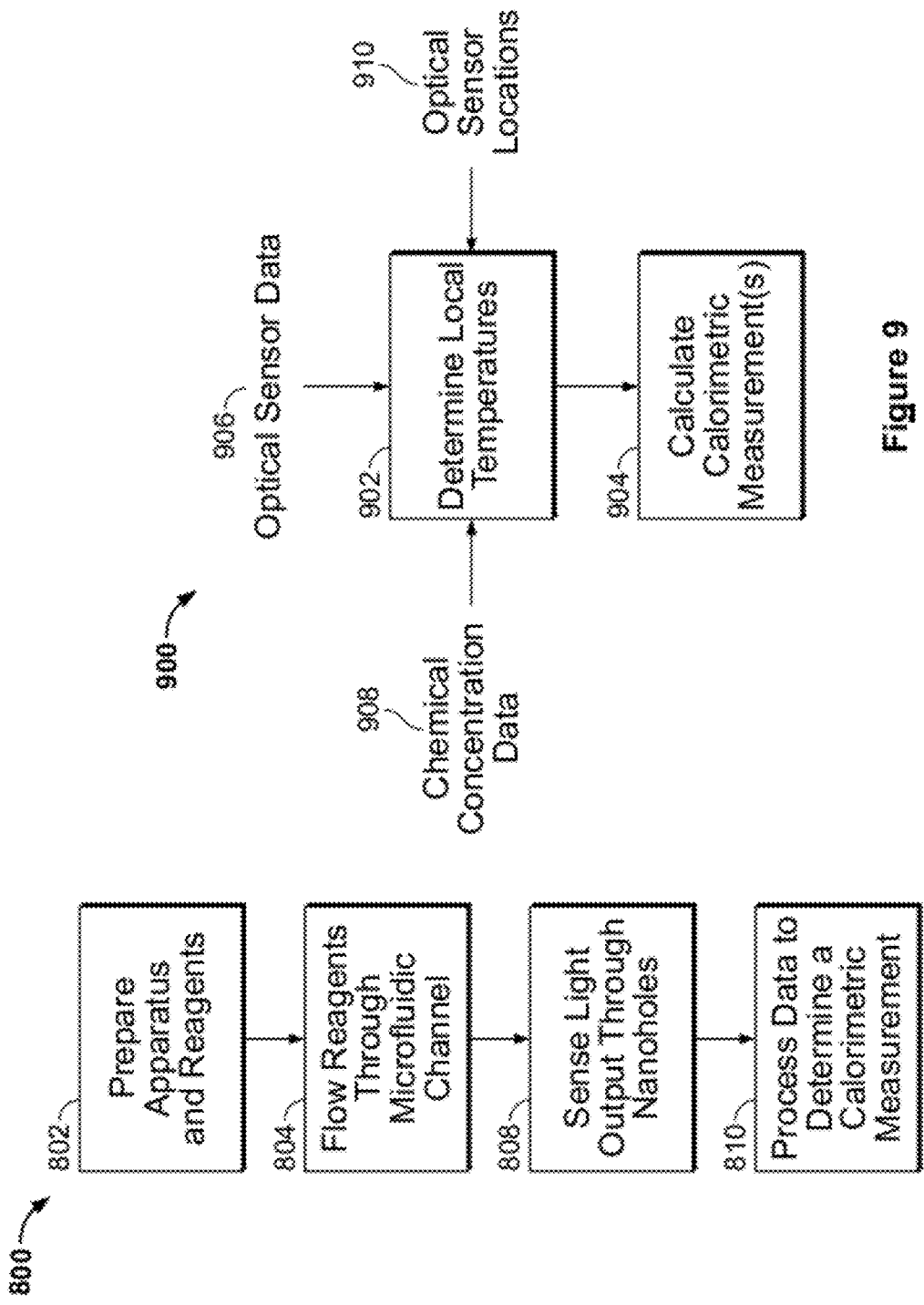

SYSTEM AND METHOD FOR A MICROFLUIDIC CALORIMETER

CROSS-REFERENCE TO RELATED APPLICATIONS

This application claims the benefit of U.S. Provisional Application No. 61/433,167, filed Jan. 14, 2011, which is incorporated by reference herein in its entirety.

STATEMENT REGARDING FEDERAL FUNDING

This invention was made with government support under Grant No. R21CA131884 awarded by the National Cancer Institute and the National Institute of Health. The government has certain rights in the invention.

FIELD OF THE INVENTION

In general, the invention relates to a microfluidic calorimetry system and a method for using a microfluidic calorimeter. More specifically, the invention relates to a system and method for providing two reagents in microfluidic laminar flow, detecting optical signals transmitted through arrays of nanoholes in a metal film, and processing the optical data to obtain a calorimetry measurement.

BACKGROUND OF THE INVENTION calorimetry is a valuable tool in pharmaceutical research and development, providing information for decision making in drug lead discovery and optimization. Unlike the present high-throughput screening methods used by the industry, such as the affinity sensors, calorimetric analysis can provide very detailed information on the binding interaction between molecules. Calorimetry provides detailed thermodynamic information including the enthalpy and entropy of a reaction. The ability to measure enthalpy and determine entropy allows the drug development team to assess the relative contributions of enthalpy and entropy to a binding reaction. Enthalpy is driven by the number and type of bonds in the binding reaction. Entropy is driven by the geometry of the ligand and the binding site. Understanding the contributions of enthalpy and entropy is critical in drug development because it allows for the selection of compounds that are more readily optimized. Specifically, reactions that are enthalpy-driven tend to be favored due to their enhanced selectivity and reactivity.

With current technology, initial high throughput screening and the first candidate drug selection is performed by affinity analysis. Only after the set of candidate drugs has been narrowed down to select few, candidates are analyzed by the two currently available calorimetry techniques, Differential Scanning calorimetry and Isothermal Titration calorimetry, to measure the thermochemical properties of a reaction. The limitations of the current generation of calorimeters include:
  Inadequate sensitivity for reactions with a low change in enthalpy
  Large amount of protein required (0.5 mg to 5 mg)
  Low experimental throughput because of both long experiment run times (60 to 90 minutes) and the need to sequentially run controls to assess the significance of the confounding effects. The potential confounding effects primarily include heating due to the mixing of dissimilar sample media (buffers with different pH, ionic strength, and solvents), the presence of DMSO from compound storage, and solvation.

Furthermore, compounds with poor solubility frequently generate hits in high throughput screens. Unfortunately, the concentrations of these compounds required to meet the mass requirement for reagents (protein and its ligand) are often above the solubility limit. As a result, calorimetry studies on the interactions of these compounds with their targets cannot be done. Paradoxically, additional synthetic/medicinal chemistry is required before calorimetry can be used, but this chemistry work cannot be justified without the calorimetry data. The outcome of this is that potentially promising compounds are not pursued. The ability to analyze smaller amounts of reagents would reduce this need for concentration.

Beyond pharmaceutical analysis, calorimetry is also valuable in many branches of materials science and chemistry. For example, calorimetry is useful for highly reactive or explosive compounds testing used in the design of chemical processes and safety equipment.

SUMMARY OF THE INVENTION

There is therefore a need in the pharmaceutical industry for a system and method for microfluidic calorimetry. Extraordinary optical transmission, a physical phenomenon, related to surface plasmon resonance, can be harnessed to produce an apparatus for determining temperature change of a chemical reaction occurring in microfluidic laminar flow. In addition to solving the aforementioned needs for such a calorimeter, the microfluidic calorimeter disclosed herein uses a stationary laminar flow with numerous benefits over traditional calorimetry methods. First, the exact volume of the reagents need not be known. Second, flowing the reagents and observing the reaction along the channel allows the reaction to be observed as it progresses, since the reagents continue to diffuse and react as they flow. Third, since the reaction and diffusion regions are stationary in space, which implies that the heat released at a location along the channel should remain constant for the duration of the test, the collected data can be integrated over time to reduce noise and error in the data.

Accordingly, systems and methods are disclosed herein for a microfluidic calorimeter apparatus. According to one aspect, a microfluidic calorimeter system includes a calorimetry apparatus and a processor in connection with the apparatus. The apparatus includes a microfluidic laminar flow channel connected to two inlets for flowing fluid into the laminar flow channel. Below the laminar flow channel is a plurality of microscale temperature sensors at known positions in the channel. The processor is in connection with the temperature sensors and determines a calorimetry measurement based on local temperatures at the respective positions of the sensors in the channel, which are based on data output by the microscale temperature sensors.

In one example, the system also includes an environmental temperature sensor that measures the temperature of the apparatus. A temperature controller receives the temperature from the sensor and heats or cools the apparatus as necessary so that the environmental temperature is nearly constant.

In one example, the temperature sensors are nanohole arrays in a metal layer below the laminar flow channel. The nanohole arrays may be surrounded by dielectric mirrors. The microfluidic calorimeter system may also include a layer between the metal layer and the laminar flow channel that transfers heat from a fluid in the laminar flow channel to the surface of the metal layer.

In one example, the system also includes a light source that directs light onto the metal layer and an optical sensor that measures light transmitted though the nanohole arrays. The optical sensor may be a photomultiplier, a charge coupled device (CCD), or a photodiode. In one example, the system includes an optical window above the laminar flow channel or forming one wall of the flow channel.

In one example, the laminar flow channel and the inlets are formed from a dielectric material. An injection valve may be connected to an inlet to introduce a reagent into a flow. The system may also include a control for varying the flow rate through an inlet.

In one example, fluid flowing into the laminar flow channel diffuses in the laminar flow channel within a stationary diffusion region. Temperature sensors may be positioned in the laminar flow channel outside of the diffusion region for measuring a baseline temperature of the non-reacting fluid. In one example, the apparatus also includes chemical sensors to detect chemical concentration in the laminar flow channel or at least one inlet.

According to another aspect, the invention relates to a method for using the calorimeter apparatus described above to determine calorimetric measurements. In one example, the method includes processing data related to the light measured from at least a subset of a plurality of aperture arrays and the respective positions of the aperture arrays in the channel. The data from the at least one optical sensor may be processed according the principles of plasmon mediated optical transmission. In one example, the method further includes disposing a reagent in a fluid so that the enthalpy associated with the reaction causes a change in temperature of the resulting solution. In one example, the method includes selecting a flow rate of a fluid based on the diffusivity of the fluid.

In one example, the chemical concentration profile is known and the optical data is deconvolved with the chemical concentration profile to determine the temperatures at the nanohole arrays. In one example, processing the data involves determining one of the binding constant of the reaction, Gibbs free energy, change in free energy, entropy, and change in entropy from the temperature.

According to another aspect, the invention relates to a method for determining a calorimetry value for a reaction. The method includes receiving optical sensor data from an optical sensor of an apparatus similar to the one described above, processing the optical data to determine a temperature change at each aperature array position along the channel, and calculating a calorimetry value from at least the temperature change, the nanohole array positions, and the flow rate, and the initial reagent concentration.

In an addition to the various examples described above, in one example, the environmental system temperature is set as reference temperature used in processing the received optical data. In another example, the temperature of the reagents outside the diffusion region is used as a baseline temperature. In one example, processing the data comprises integrating the data over time.

According to another aspect, the invention relates to a disposable calorimetry apparatus comprising a microfluidic laminar flow channel connected to two inlets for flowing fluid into the laminar flow channel. Below the laminar flow channel is a metal film layer with a plurality of nanoholes at known positions in the channel. In addition to various examples described above with respect to the laminar flow channel, inlets, and metal film layer, in one example, the apparatus is multiplexed. In this example, the disposable apparatus further comprises at least a second laminar flow channel and metal layer. An experiment performed in a first laminar flow channel can differ from an experiment performed in a second laminar flow channel in at least one of environmental temperature, a reagent material, a solvent material, a reagent concentration, and a reagent flow rate.

According to another aspect, the invention relates to a method for pharmaceutical development that generates optical sensor data for a plurality of reactions between a drug and another protein using at least one of the calorimetry apparatuses described above. The method further includes determining a calorimetry measurement for each reaction and selecting one of the drugs for further clinical investigation.

According to another aspect, the invention relates to a system for temperature sensing comprising a microfluidic laminar flow channel connected to two inlets for flowing fluid into the laminar flow channel and at least one discrete temperature sensing device positioned along the laminar flow channel.

BRIEF DESCRIPTION OF THE DRAWINGS

The patent or application file contains at least one drawing executed in color. Copies of this patent or patent application publication with color drawings will be provided to the Office upon request and payment of the necessary fee. The above and other features of the present invention, its nature and various advantages will be more apparent upon consideration of the following detailed description, taken in conjunction with the accompanying drawings in which:

The system and method may be better understood from the following illustrative description with reference to the following drawings in which:

FIG. 8 is a flowchart for a method of using the microfluidic calorimetry system of FIG. 1, according to an illustrative embodiment of the invention;

FIG. 9 is a flowchart for a method of processing optical data received from the microfluidic calorimetry system of FIG. 1 to obtain calorimetric measurements, according to an illustrative embodiment of the invention;

DESCRIPTION OF CERTAIN ILLUSTRATIVE EMBODIMENTS

To provide an overall understanding of the invention, certain illustrative embodiments will now be described, including systems and methods for microfluidic calorimetry. However, it will be understood by one of ordinary skill in the art that the systems and methods described herein may be adapted and modified as is appropriate for the application being addressed and that the systems and methods described herein may be employed in other suitable applications, and that such other additions and modifications will not depart from the scope thereof.

Figure 1:
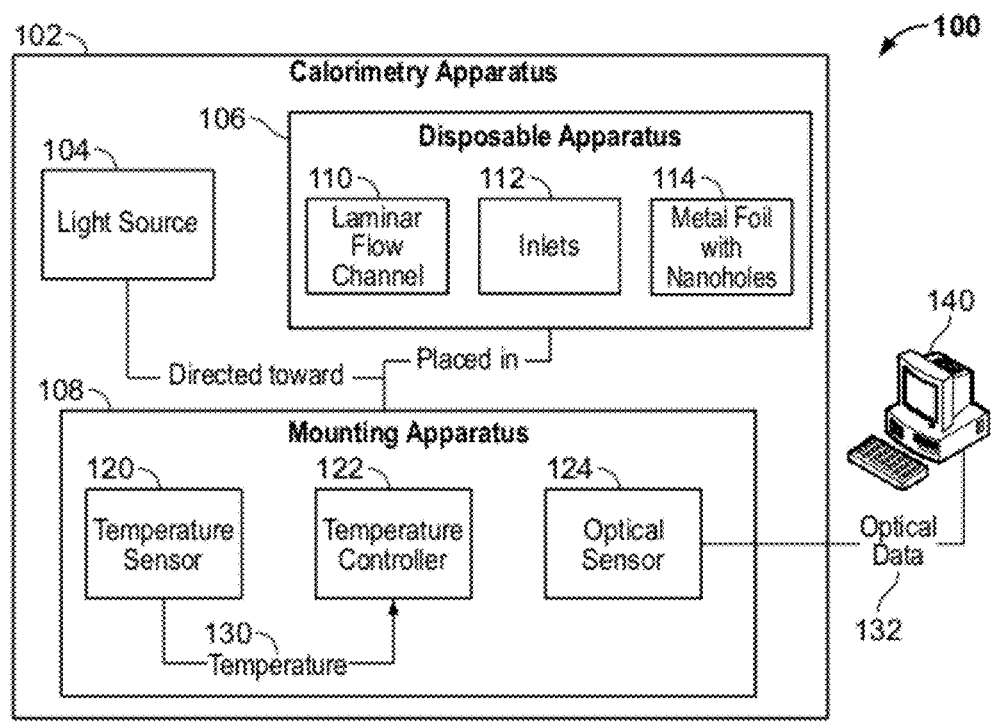
FIG. 1 is block diagram of a system for microfluidic calorimetry, according to an illustrative embodiment of the invention.

FIG. 1 is a block diagram of a system for microfluidic calorimetry 100, according to an illustrative embodiment of the invention. The system 100 is used to detect temperature change and other calorimetry measurements from a microscale chemical reaction. A user runs an experiment in the microfluidic calorimeter by flowing two reagents into and through a laminar flow channel, causing the reagents to react at their diffusion interface. An optical sensor detects Extraordinary Optical Transmission (EOT) signals, which are affected by the temperature change of the flowing solution due to the reaction. The EOT signals are emitted through nanoholes in a metal film below the laminar flow channels. A computer processes the EOT signals to obtain the temperature change and other calorimetric measurements.

The system consists of a calorimetry apparatus 102 and a processor 140. The calorimetry apparatus 102 consists of a light source 104, a disposable apparatus 106, and a mounting apparatus 108. The disposable apparatus consists of a laminar flow channel 110, inlets 112, and a metal foil with nanoholes 114. The two reagents enter the laminar flow channel 110 from inlets 112. The arrangement of the laminar flow channel and inlets will be discussed in more detail with respect to FIG. 5. Below the laminar flow channel is a metal foil 114 with a plurality of arrays of nanoholes used in optical transmission sensing. The heat of the liquid in the laminar flow channel 110 directly above the nanohole arrays affects the surface plasmon resonance (SPR) in the metal foil, which thereby affects light transmission through the nanoholes. The principles of nanohole array sensing are discussed in greater detail with respect to FIGS. 3 and 4.

The disposable apparatus 106 is placed in a mounting apparatus 108 which consists of a temperature sensor 120, a temperature controller 122, and an optical sensor 124. The temperature sensor 120 and temperature controller 122 are used to maintain a fairly constant system temperature to prevent environmental temperature fluctuations from impacting the experiment. The temperature sensor 120 detects the environmental system temperature 130 and sends it to the temperature controller 122. Based on the current environmental system temperature 130, the temperature controller 122 either heats or cools the system, or takes no action if the temperature is near enough to the set temperature. In one embodiment, the environmental temperature is permitted to vary by 0.0002° K., but depending on the amount of heat released by the reaction, the required accuracy, and the precision of the temperature sensor, the environmental temperature may be held within smaller or larger ranges. The temperature 130 may also be sent to the system processor 140 for use in calibration of the calorimetry apparatus or for use as a reference temperature in calculating calorimetric values.

The optical sensor 124 detects light emitted through the nanoholes in the metal foil 114. The optical sensor 124 may be a photomultiplier, a photodiode, a charge-coupled device (CCD) or other image sensor, or any other apparatus capable of detecting light with sufficient sensitivity to distinguish nanohole arrays from one another. The optical sensor sends the optical data received through the nanoholes to processor 140.

The calorimetry apparatus 102 also includes a light source 104 which emits light directed toward the metal film with nanoholes 114. In one embodiment, the light source 104 emits light which travels through the laminar flow channel 110 and onto the metal foil at incident angle θ. The light source may be a single wavelength laser. Alternatively, the light source may be a broadband source, and a monochromator or optical filters may be used to deliver a monochromatic beam of light, or spectrometry techniques may be used in detection.

Figure 2:
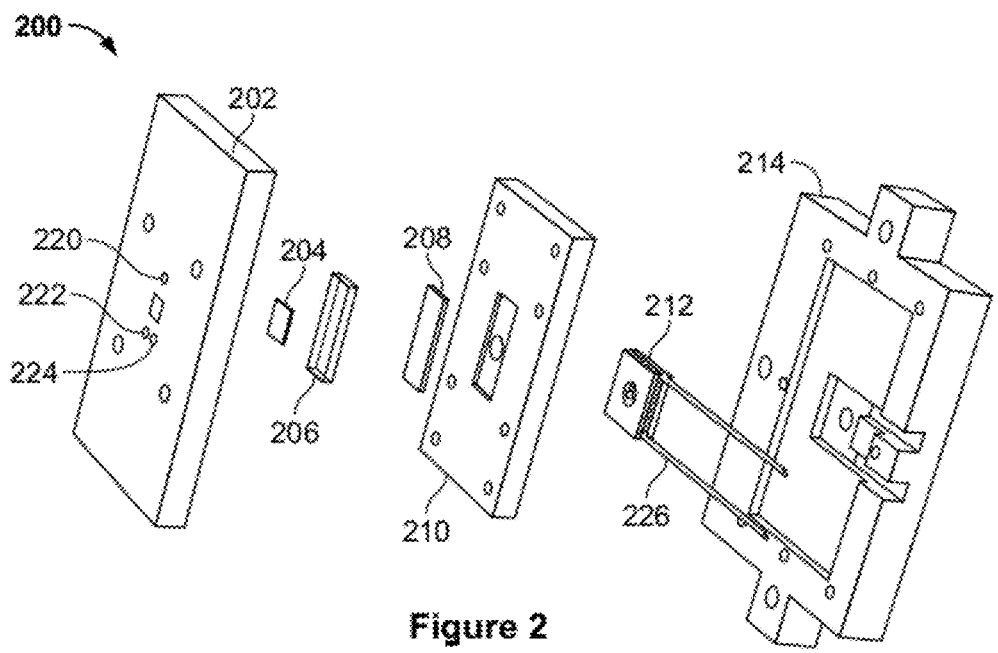
FIG. 2 is an exploded solid model of an apparatus for use in a system of microfluidic calorimetry, according to an illustrative embodiment of the invention.

FIG. 2 is an exploded solid model 200 showing parts of the mounting apparatus 108 and the disposable apparatus 106 in an exemplary embodiment of a system for microfluidic calorimetry. From left to right, the solid model 200 depicts a plastic cover 202, coverglass 204, flow cell 206, nanohole array chip 208, mounting tray 210, heating unit 212, and plastic base 214. The plastic cover 202, mounting tray 210, and plastic base 214 support and protect the apparatus. They are the main structural components of the mounting apparatus 108. Flow cell 206, part of the disposable apparatus 106, contains features that comprise walls of the laminar flow channel 110 and the inlets 112. The flow cell 206 is molded from a polydimethylsiloxane (PDMS) mixture that insulates the flow cell from the top, but another similarly insulative material that can be molded with sufficient precision may be used. A 3D solid object printer may fabricate a mold used to create the PDMS flow cell. Alternatively, photolithography may be used to form the flow cell 106. The access holes 220, 222, and 224 allow tubing access to the flow cell. Access hole 220 provides access to the laminar flow channel 110 so that fluids may be removed after flowing through the flow channel, and access holes 222 and 224 provide access to the two inlets to introduce reagents into the inlets. The tubing that enters the inlets 112 through the access holes 222 and 224 connect to a means of controlling injection volume and speed into the inlets 112, such as syringes with syringe pumps. The mounting elements 202, 210, and 214 may be constructed using a 3D solid object printer or other suitable manufacturing method. After assembling the calorimetry apparatus, the plastic cover 202 and plastic base 214 are tightened using screws or other clamp assembly, not shown, to hold the elements in contact with each other.

The nanohole array chip 208 consists of a conductive surface, in this case the metal foil with nanoholes 114, atop a transparent surface, such as a glass substrate, which also serves as an insulator. The types and properties of suitable metals for use in nanohole sensing and further details about designing and producing nanohole array chips are discussed in U.S. Pat. No. 7,318,907, the contents of which are incorporated herein in its entirety. In an exemplary embodiment, a thin (e.g. 25 nm) layer of chromium or other metallic bonding agent is first evaporated onto the glass substrate. A thicker (e.g. 105 nm) layer of gold is then evaporated atop the chromium. In the alternative, the metal foil could be made of gold, silver, aluminum, beryllium, rhenium, osmium, potassium, rubidium, cesium, rhenium oxide, tungsten oxide, copper, titanium, or another suitable metal. Once the metals have been deposited, nanohole arrays are milled into the metal using, for example, photolithographic techniques, electron beam lithographic techniques, a focused ion beam (FIB), or other methods. For a FIB with a current of 1 pA, 15 seconds is necessary to mill through the metal layers. As depicted in FIG. 1, the nanohole array chip 208 may be part of the disposable apparatus. The nanohole array chip 208 may be attached to the flow channel, or it may be a separate disposable part that mounting tray 210 aligns with the mounting apparatus 108. In this embodiment, the fluids in the laminar flow channel 110 directly contact the metal foil when the apparatus is assembled and clamped.

Heating unit 212 consists of a thermoelectric heater and at least one temperature sensor, such as a thermistor. Wires 226 connects the heating unit 212 to a heat controller (not shown), which controls the thermoelectric heater based on the temperature from the thermistors. The heating unit 212 may also be able to cool the apparatus. Optical sensor 124, not shown on FIG. 2, is below the plastic base 214. The heating unit 212 and mounting elements 210 and 214 have holes in their center so that light passing through the nanoholes can reach and be measured by the optical sensor 124. The hole in the heating unit does not substantially affect the temperature consistency throughout the laminar flow channel 110.

The disposable apparatus 106 may contain at least a second laminar flow channel (not shown) that may be fluidly connected to the same set of inlets or to one or more additional inlets for a multiplexed design that permits more than one experiment on a single chip. Another set of nanohole arrays on the metal foil 114 or a second metal foil is below the second laminar flow channel. The mounting apparatus may be configured to run multiple experiments at the same time or perform experiments one at a time. If experiments are to be performed one at a time, the mounting apparatus may have a single optical sensor that moves from flow cell to flow cell as tests are run at each flow cell. An experiment performed in one laminar flow channel in the multiplexed apparatus could differ from an experiment performed in a different laminar flow channel in at least one of environmental temperature, a reagent material, a solvent material, a reagent concentration, and reagent flow rate.

Figure 3:
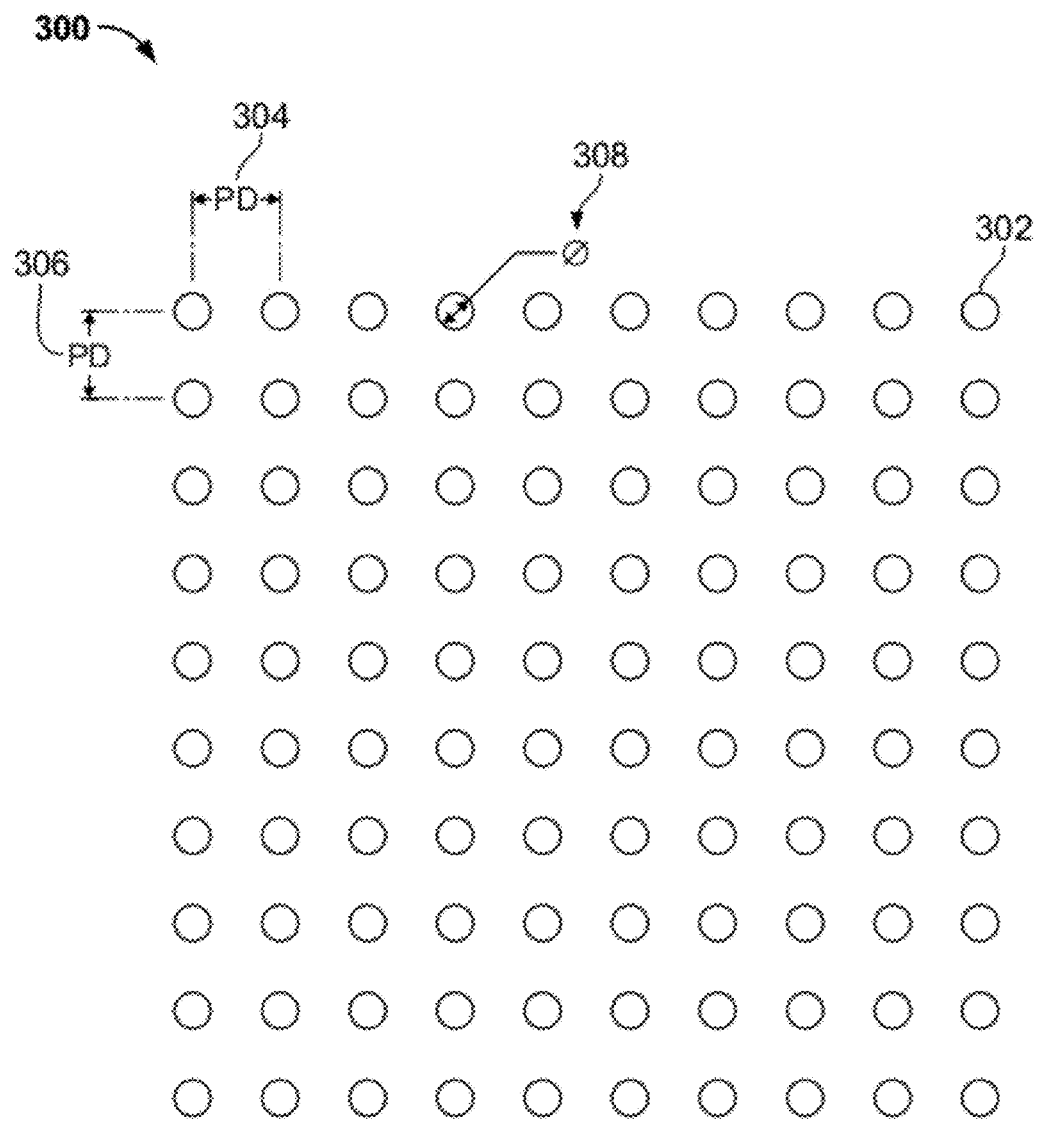
FIG. 3 is a diagram of an array of nanoholes used for optical transmission, according to an illustrative embodiment of the invention.

FIG. 3 is a diagram of a single ten-by-ten nanohole array 300. The interaction of incident light from the light source and surface plasmon resonance (SPR) excited by the light source causes extremely efficient light transmission through the nanoholes, called extraordinary optical transmission (EOT). Previous studies and experimental results have shown that the behavior of EOT signal due to changes in concentration or temperature is dependent on a variety of nanohole parameters, such as diameter of the nanoholes, shape of the nanoholes arrangement (e.g. rectangular vs. circular arrangements), size of the nanohole array, positioning of the nanohole arrays, etc. In this embodiment, the nanohole array 300 is formed of 100 nanoholes 302 positioned in a square, but the number and arrangement of nanoholes may be different; for example, three-by-three and nine-by-nine nanohole arrays are also commonly used. The nanoholes may be arranged in a different pattern, such as a hexagonal, linear, or bull's eye pattern. The pitch distances 304 and 306 between the nanoholes, measured from the center of one nanohole to the center of a neighboring nanohole, are labeled PD. The horizontal pitch distance 304 and vertical pitch distance 306 are the same. In one embodiment, the pitch distance PD is 350 nm, and diameter of each nanohole 308 is 150 nm (Ji et al., 2008). The choice of 150 nm is decided by the easy fabrication of relatively large holes using Focused Ion Beam (FIB) and electron-beam lithography (Ji et al., 2008). The hole diameter may range from 130 nm to 290 nm, or smaller holes may be used. The pitch distance is dependent on the wavelength of the incident light, the geometric pattern of nanoholes, and the dielectric constants of the metallic film and the solvent above the metallic film. Pitch distance may range from 220 nm to 540 nm. The pitch is a function of the wavelength of the light being used and the geometric pattern being used.

Each nanohole array 300 may be surrounded by dielectric mirrors, such as Bragg mirror groves, to reflect and confine the surface plasmon energy associated with a transmission peak of the nanohole array. This creates both constructive and destructive interference effects, thereby enhancing or decreasing the transmission at certain wavelengths. Use of Bragg mirrors for nanohole sensing applications is discussed in greater detail in Lindquist et al. (2009), the contents of which are incorporated herein in its entirety.

Figure 4A:
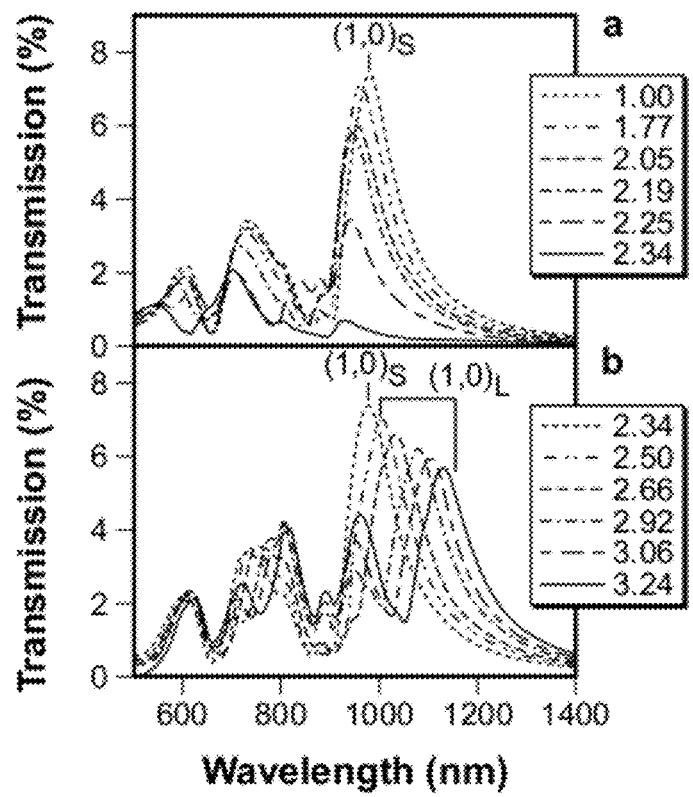
FIG. 4a is a graph of optical transmission versus wavelength for multiple dielectric constants through an exemplary array of nanoholes.

The percentage of transmitted light in EOT transmission is affected by the wavelength of the incident light, as shown in FIG. 4a, which shows the transmission percentage versus wavelength for multiple fluid dielectric constants (Krishnan, A. et al. 2001). For a particular dielectric fluid layer with dielectric constant $\epsilon_1$ and a metal foil with dielectric constant $\epsilon_2$, light having angle of incidence θ, metal foil having lattice constant $a_0$, and a constant γ, the resonance wavelength peak is as follows:

$$\lambda_{peak} = \frac{a_0}{\gamma}\left[\left(\frac{\varepsilon_1 \varepsilon_2}{\varepsilon_1 + \varepsilon_2}\right)^{\frac{1}{2}} - \sin\theta\right] \qquad (1)$$

Equation 1 indicates that a change in resonance wavelength at a peak is based on the change in the dielectric constant of the dielectric fluid layer, as all other variables are constant during a chemical reaction observed in the calorimetry system. The change in dielectric constant depends on changes in temperature, pressure, and concentration of a material. Relating the dielectric constant to changes in temperature and pressure, while holding concentration constant and defining:

$$\Phi = \frac{\rho}{\rho_0} = \exp\{-[\beta(T - T_0) - k_T(P - P_0)]\}$$

wherein ρ is density, T is temperature, β the coefficient of volumetric expansion, T is temperature, $k_T$ is the isothermal compressibility factor, and P is pressure, gives:

$$\lambda_{peak} = \frac{a_0}{\gamma}\left[\left(\frac{\varepsilon_2\left[\frac{1 + 2C_0\rho_0\Phi}{1 - C_0\rho_0\Phi}\right]}{\left[\frac{1 + 2C_0\rho_0\Phi}{1 - C_0\rho_0\Phi}\right] + \varepsilon_2}\right) - \sin\theta\right] \qquad (2)$$

wherein constant concentration $$C_o = \left[\frac{n_o^2 - 1}{n_o^2 + 2}\right](1/\rho_o),$$

and $n_0$ and $\rho_0$ are the values for reference temperature and pressure conditions. As shown in FIG. 4a, experimental results show that as the dielectric constant $\in_1$ of the fluid changes, both the peak wavelength and the percentage of transmission at the peak wavelength changes. Moreover, for a single wavelength, transmission percentage, which is measured by the optical sensor 124, changes as the dielectric constant of the fluid changes.

Figure 4B:
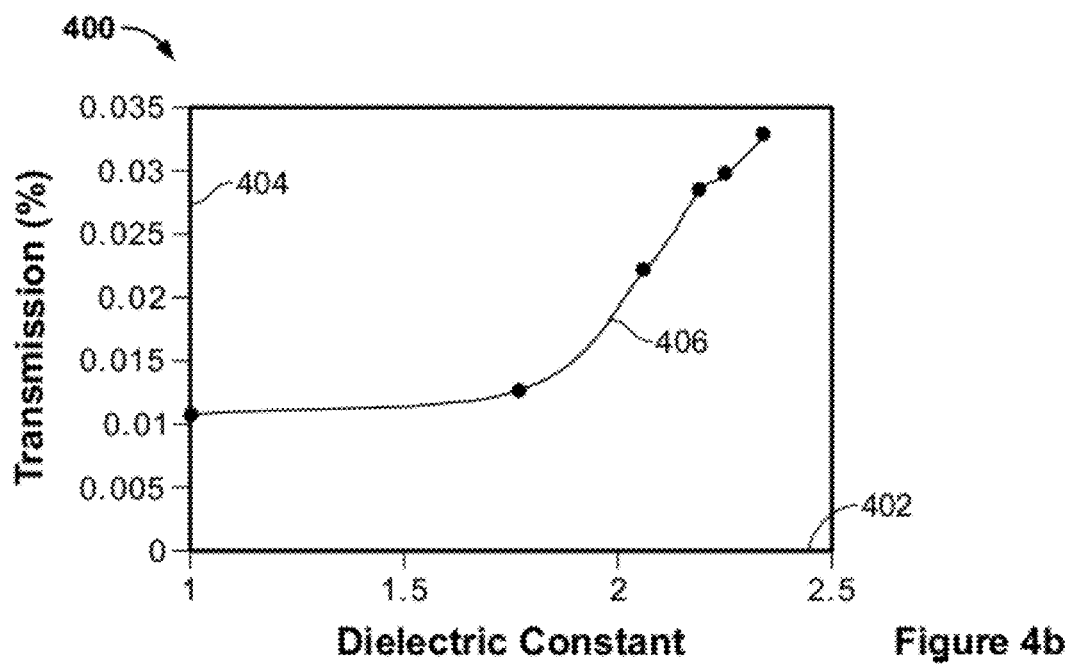
FIG. 4b is a graph of optical transmission versus dielectric constant through an exemplary array of nanoholes.

This is more clearly shown in FIG. 4b, a graph showing percentage of incident light transmitted through a subwavelength nanohole array versus the dielectric constant of the material adjacent to the nanoholes (Krishnan, A. et al. 2001). Since the dielectric constant depends on the temperature, pressure, and concentration of the material, an EOT sensor can therefore be used as a temperature sensor.

Figure 5:
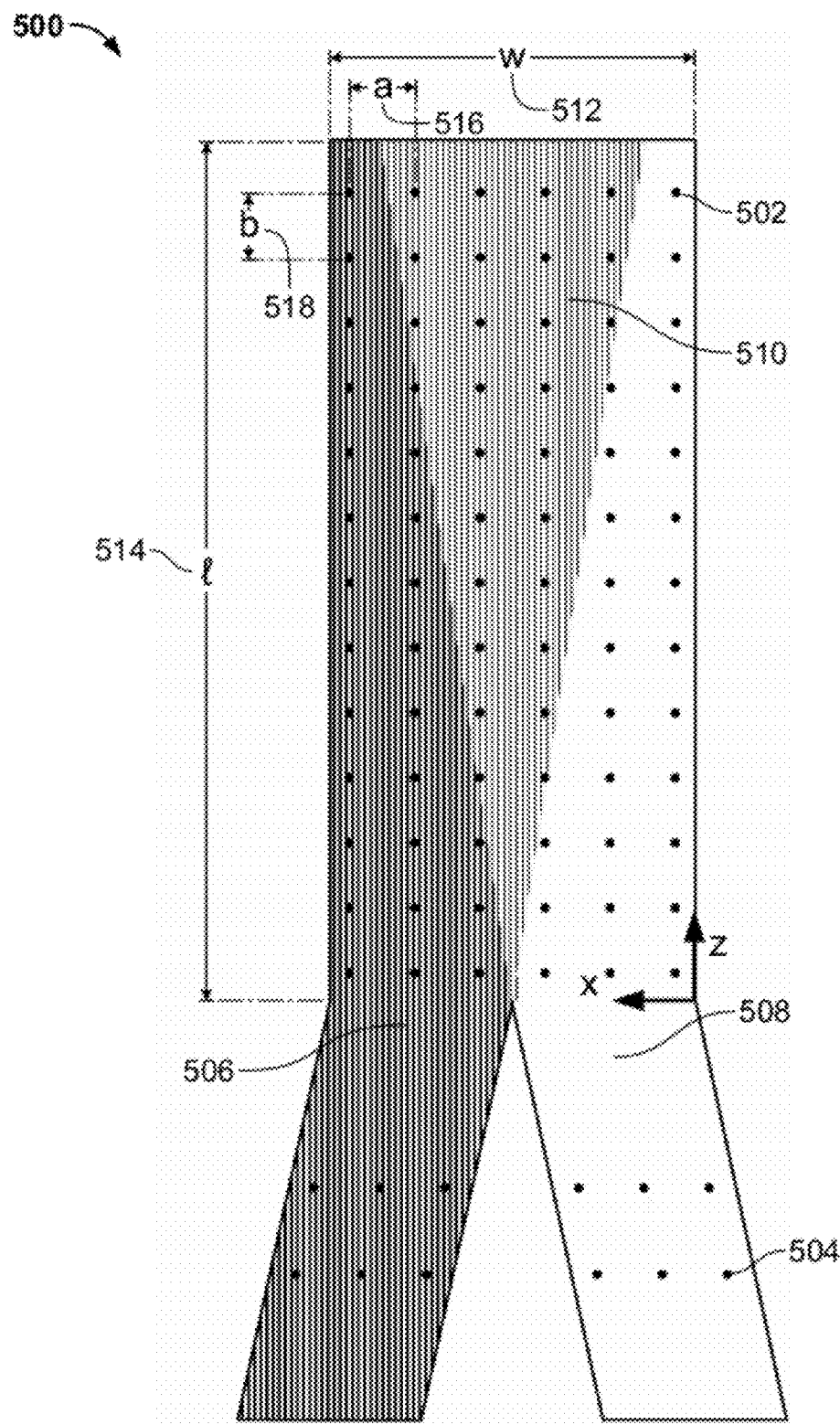
FIG. 5 is a diagram of laminar flow channel with inlets and nanohole arrays, according to an illustrative embodiment of the invention.

FIG. 5 is a diagram of laminar flow channel 110 and inlets 112 with nanohole arrays 502 and 504, according to an illustrative embodiment of the invention. Flow is fully developed in the channel and is at steady state condition. The left inlet contains a first reagent 506, shown in a dark stripe. The right inlet contains a second reagent 508, shown in solid white. For an exemplary pharmaceutical test, the fluid flowed through one inlet contains a drug and the fluid flowed through the other inlet includes a protein to which the drug may or may not bind. Other kinds of reagents may be used for other types of calorimetry studies. The lighter striped region 510 shows the diffusion region at the interface of the two reagents in which the reaction is occurring. The shape of this diffusion region will depend on the flow rates of the reagents and the diffusivity of the fluids; more diffusive reagents or will have a wider diffusion region than less diffusive reagents. The reagents may be given two different flow rates to control the shape or position of the region. An acceptable range for the flow rate in the channel is from 0.0005 m/s to 0.05 m/s, or from 0.15 μL/min to 15 μL/min. Although for illustration the inlets in FIG. 5 are shown entering the laminar flow channel at an angle, it is preferable that before entry into the laminar flow channel they are substantially parallel to each other and in line with the laminar flow channel so that the fluids have no x-velocity upon entering laminar flow.

The diffusion region 510 is stationary over time, providing several key advantages over traditional calorimetry methods. As reagent volume is added to the channel, reagents continue to flow through the channel so at a given nanohole under the diffusion region 510 the fluid above it has a substantially similar concentration and heat of reaction for the duration of the test. This allows an observer to integrate the data over time, reducing noise and error in the measurements. Additionally, since the diffusion region is spread out along the length of the channel, multiple stages of the reaction are observed simultaneously, allowing detailed observations for how the reaction progresses with time. Furthermore, since the ratio of the left reagent to the right reagent varies across the width of the diffusion region, nanoholes across the width of the channel observe the reaction with varying relative concentrations of reagents.

The width of the laminar flow channel 512, labeled w, and length of the channel 514, labeled l, are not to scale, as the length l is typically much longer than the width w. In one embodiment, w is 500 μm and length is 5000 μm to provide a sufficiently large surface area to observe substantial interdiffusion of reagents and generation of reaction products. More generally, the width could be typically in the range of 50 to 1000 μm, and the length could be in the range of about 500 to 10000 μm. The channel width and length are bounded from above by the desired reagent volume consumed and by the need to maintain laminar flow, and from below by the minimum separation of nanohole arrays and desired resolution of nanohole arrays, i.e. the number of nanohole array sensors.

The height of the laminar flow channel, in one embodiment, is 10 μm, but may be typically in the range of 1 to 30 μm. A smaller height will reduce reagent volume consumed and may improve accuracy and sensitivity, since variations in temperature across the height of the channel will be minimized. However, practical considerations such as fabrication tolerances and inlet pressure may set a lower bound on channel height. Reagent volumes consumed are determined by the internal geometric volume of the laminar flow channel. The reagent volume of each of the two components will be at least equal to one half the product of the length, width, and height of this channel. In practice, typically 2 to 10 times this product will be needed to stabilize flow and perform a measurement. Other considerations in designing the laminar flow channel are the flow rates needed for laminar flow and the diffusivity of the reagents. The channel width and length will vary depending at least on these characteristics. Nanohole arrays 502 are equally spaced horizontally by distance 512, labeled a, and vertically by a distance 518, labeled b. As shown, a and b are equal, but they need not be. Furthermore, the nanohole arrays 502 need not be equally spaced throughout the laminar flow channel 110. For example, in the horizontal direction, nanohole arrays 502 may be more concentrated near the center of the channel where the reagents are reacting. In the vertical direction, nanohole arrays 502 may be concentrated near the inlets 112 where the reagents begin to react. While placing nanohole arrays 502 near the reaction is important to capture the temperature change, it may also be useful to place nanohole arrays 502 near the edges of the laminar flow channel 110 to take baseline measurements of the fluids whose temperature has not been affected by the reaction. Similarly, it may be useful to place nanohole arrays 504 or other types of temperature or concentration sensors in the inlets 112 to take baseline measurements of the reagents before any reaction or diffusion. One method for determining spacing of the nanoholes 502 in the laminar flow channel is discussed in more detail with respect to FIG. 10.

Figure 6A:
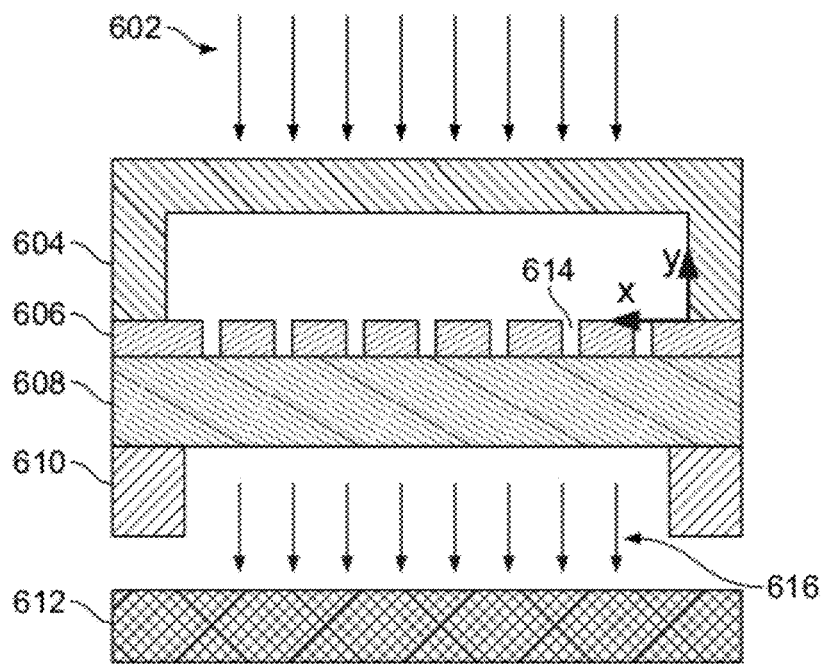
FIGS. 6a, 6b, and 6c are section views of a laminar flow channel for use in a system of microfluidic calorimetry, according to various illustrative embodiments of the invention.

FIG. 6 shows various section views of laminar flow channels for microfluidic calorimetry. FIG. 6a shows laminar flow channel 600 consisting of PDMS channel 604, metal foil 606 with nanoholes 614, glass substrate 608, heating unit 610, and optical sensor 612. Reagents travel through the rectangle bounded by the PDMS channel 604 and the metal foil 606. Incident light 602 travels into the channel through the PDMS layer 604, hitting the metal foil 606. This excites surface plasmons at the top of the metal foil, which interact with the light creating EOT 616 that travels through the glass substrate 608 and to the optical sensor 612. As mentioned previously, the optical sensor may be a photomultiplier, a photodiode, a charge-coupled device (CCD) or other image sensor, or any other apparatus capable of detecting light with sufficient resolution to distinguish nanohole arrays from one another. Heating unit 610, similar to heating unit 212, again does not interfere with the EOT 616. The elements of the laminar flow channel and other equipment are not to scale.

Figure 6B:
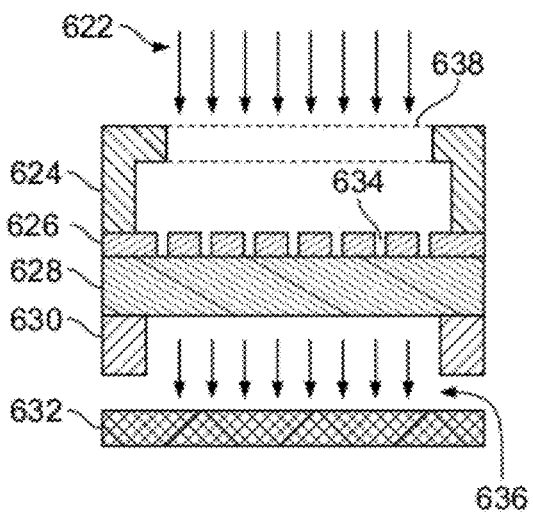

FIG. 6b is similar to FIG. 6a, but it includes optical window 638 at the top of the laminar flow channel. This allows the reaction to be observed from above. It also allows the sides of the laminar flow channel to be constructed by a material, such as a silicate, that would otherwise interfere with the light source, as the light source would travel through the optical window rather than through the interfering material. Access to alternate materials for manufacturing the flow channel allows greater design precision and therefore a smaller laminar flow channel volume with more material options.

Figure 6C:
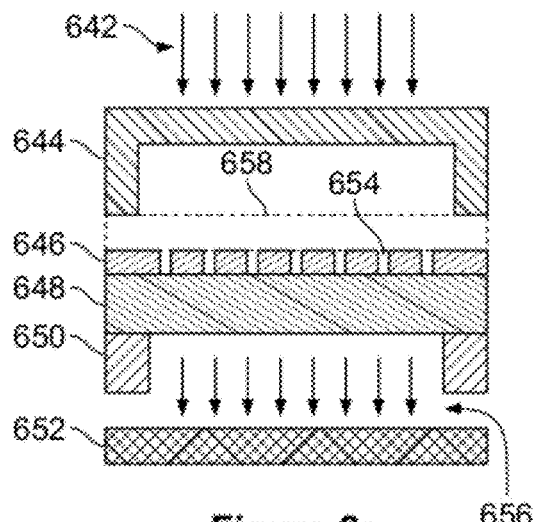

FIG. 6c is also similar to FIG. 6a, but in this case laminar flow channel 660 also contains a dielectric heat transfer layer 658 disposed above the metal foil 646 and below the PDMS channel 644. As the nanohole arrays can only sense temperature changes a very small distance above their surface, e.g. 100 nm, the heat of the reaction must travel through the heat transfer layer 658, or the heat transfer layer must be extremely thin. If the glass substrate coated in the metal foil is to be reused for more than one calorimetry test, the heat transfer layer 658 would be part of the disposable apparatus 106 from FIG. 1 to protect the reusable metal foil from the reagents and the reaction. Layer 658 may be composed of, for example, vapor deposited silicon dioxide, silicon nitride or spin coated or vapor deposited polymers such as PDMS, acrylic, or polycarbonate.

Figure 7:
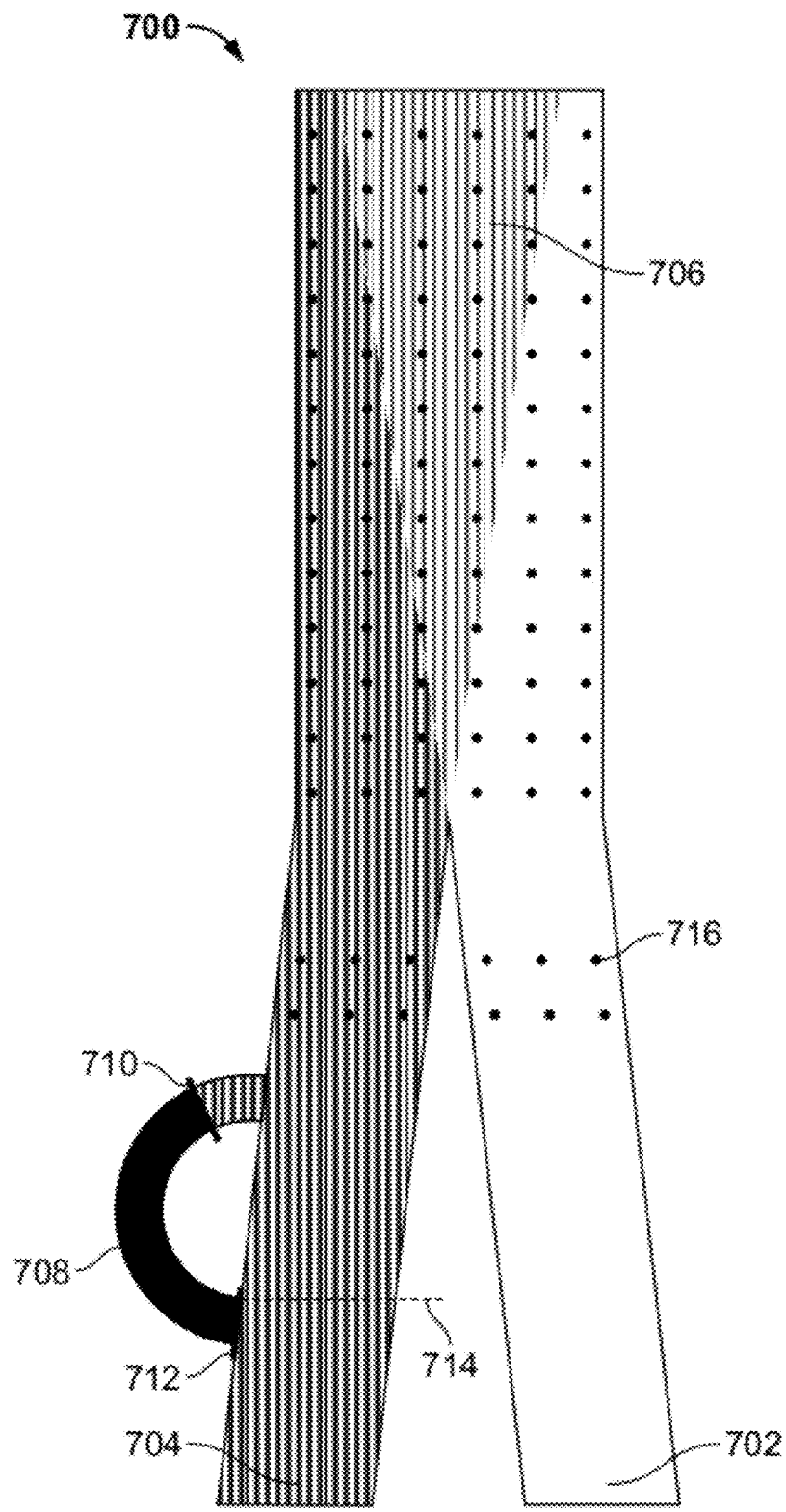
FIG. 7 is a diagram of a laminar flow channel with an injection valve for use in a system of microfluidic calorimetry, according to an illustrative embodiment of the invention.

FIG. 7 shows a laminar flow channel 110 with inlets 112 in which the left inlet includes an injection valve. The left inlet contains a first fluid 704, shown in a dark stripe. The right inlet contains a second fluid 702, shown in white. The lighter striped region 706 shows the diffusion region at the interface of the two reagents. As in FIG. 5, the shape of this diffusion region will depend on the flow rates of the reagents and the diffusivity of the fluids. The left inlet includes an injection valve that stores reagent 708. Fluid 704 is a buffer fluid used to initialize flow through the laminar flow channel. Any suitable aqueous buffer, preferably an optically clear buffer with dielectric properties that are sensitive to temperature, is suitable. Baseline measurements may be taken and/or calibrations performed while the buffer fluid 704, which does not react with the right fluid 702, is flowing. After a laminar flow has been initialized, the injection valve will release reagent 708. The injection valve is used to minimize the amount of the reagent 708 used in a calorimetry test, especially if the reagent is scarce or expensive. In one embodiment, the reagent 708 is a protein solution, and the right inlet contains a drug, but other reagents may be used for other applications, such as enzymological studies, combustion, control systems, temperature compensation circuits, and the study of explosives. In another embodiment, both left and right inlets contain buffer solution, and both left and right inlets have injection valves for simultaneously injecting two reagents.

This simplified diagram of an injection valve includes reagent gate 710 that blocks the reagent 708, valve gate 712 that blocks flow into the valve, and inlet gate 714 that, when closed, forces the reagent out of the valve and into the laminar flow channel to react with the right fluid 702. At the start of an experiment, gates 710 and 712 are closed and inlet gate 714 is open, as shown in FIG. 7, so that the reagent stays in the valve while buffer fluid 704 travels through the left inlet. Once laminar flow has been established, the inlet gate 714 closes while gates 710 and 712 open, causing the buffer fluid 704 to move into the injection valve, forcing the reagent 708 out of the valve and into the inlet. Ideally, changing the path of the fluid flow does not disrupt the fluid pressure into the laminar flow channel, which may disrupt the laminar flow. Even after the reagent 708 has been released, flow continues through the injection valve pathway so that the pressure of the fluid behind the reagent is not disrupted.

In this embodiment, the reagent 708 may mix with the buffer solution 704 as it leaves the valve. The inlet gate 714 may even remain slightly open to allow the buffer flowing past gate 714 to mix with the reagent as it exits the injection valve. In this case, the nanoholes 716 can be used to measure the EOT signals of the reagent solution and determine its concentration. Alternatively, an injection valve configuration may prevent the reagent from mixing with the buffer solution. Pumps may be used in an injection system to regulate flow; for example electrokinetic injection systems and peristaltic injection systems may be used, or any other microscale injection system, such as the injection flow system disclosed in Leach, et al. (2003), the contents of which are incorporated herein in its entirety. In one multiplexed embodiment, multiple injection valves are placed on a single inlet so that multiple tests may be run through the same laminar flow channel.

FIG. 8 is a flowchart for a method of using a microfluidic calorimeter, especially the calorimeter of FIG. 1. First, the apparatus and reagents are prepared (Step 802). This may include putting reagents into injection valves, as discussed with respect to FIG. 7, and further preparing buffer fluids. Reagents may be dissolved into or mixed with a solvent. In this case, the heat of the chemical reaction will cause a detectable temperature change in the fluid. Preparing the apparatus includes assembling calorimetry apparatus, e.g. by inserting the disposable apparatus including at least the inlets and laminar flow cell into the mounting equipment so that the optical sensor, nanoholes, and laminar flow channel are properly aligned, with the heating unit in place and not disrupting the path of the light. As applicable, preparation also includes aligning the light source so that it is directed at the nanoholes and, if entering the laminar flow channel from above, the angle of incidence is known. Any tubing to external fluid sources or injection valves is connected. Finally, wiring to an external heat controller and a computer for receiving and processing the data is connected as needed.

Next, the reagents are flowed through the microfluidic channel (step 804). The flow rates are selected prior to beginning the test, and they are controlled by the injection system, which includes the injection mechanism for the buffer solution and any injection valves. Alternatively, the flow rates may be adjusted and/or other calibrations performed as the buffer solution is passing through the laminar flow channel. If both inlets are connected to injection valves that inject the sample after initialization with a buffer solution, release of the reagents from the injection valves must be carefully controlled so that both reagents occupy the laminar flow channel simultaneously.

Once fluids are flowed into the laminar flow channel, the optical sensor senses the light output through the nanoholes and sends the data to a connected computer processor (step 806). The computer processor then processes at least the light emission data to determine a calorimetric measurement of the reaction (step 808). The data processing to determine calorimetric measurements is discussed with respect to FIG. 9.

FIG. 9 is a flowchart for a method of processing optical data to obtain calorimetric measurements. The computer receives optical data 906 from the optical sensor. Also, the computer has in memory or receives the locations of the optical sensors 910 along the channel. The optical sensor data depends on both concentration and temperature in the relationship $D=TC+Error$, wherein D is a matrix of the optical data over space, T is the temperature matrix, which is convoluted with concentration matrix C, and the error term is experimental measurement noise. Multivariate curve resolution alternating least squares (MCR-ALS) is a deconvolution technique that may be used to iteratively calculate concentration and temperature to best fit the experimental data within given constraints, such as non-negativity, closure, or other hard modeling constraints. Other suitable iterative or non-iterative deconvolution methods may be used. Since the optical data depends on both the concentration and temperature of the fluid, information about the chemical concentration 908 is preferably known in order to determine fluid temperature at the nanosensor array locations from the optical data (step 902). Since the reagents are in laminar flow undergoing diffusion, known mass transport properties of the reagents may be used to determine an initial guess for concentration used as in the deconvolution algorithm to determine temperature. Additionally, nanohole arrays in the laminar flow channel or in the inlets may be used as chemical concentration sensors in locations where the temperature is known. Alternatively, other types of chemical concentration sensors may be placed along the laminar flow channel or inlets to directly measure the concentration. Since the diffusion region is stationary in space, the temperature map and optical data should be stationary over time. Therefore, in order to reduce the noise term, the data may be integrated over time.

Once the local temperatures have been determined, other calorimetric measurements may be calculated (step 904). The x and z directions are shown in FIG. 5 at the initial intersection of fluids 504 and 506. The origin (x=0; y=0; z=0) is where the right edge of the right inlet meets the laminar flow channel in the plane of the top of the metal foil. The x and y directions are shown in FIG. 6a. The formulation for the energy equation in the channel is as follows, wherein $\rho$ is density of the fluid, c is specific heat of the fluid, $V_z$ is the speed along the channel in the z direction, T is temperature, k is the thermal conductivity of the solution flowing in the channel, and q is the heat release or absorption due to the reaction:

$$\rho c V_z \frac{\partial T}{\partial z} = k\left(\frac{\partial^2 T}{\partial x^2} + \frac{\partial^2 T}{\partial y^2} + \frac{\partial^2 T}{\partial z^2}\right) + \dot{q}(x, y, z) \quad (3)$$

Integrating in y-direction over a channel depth d (y=0 to y=d) and defining $$\overline{T} = \frac{1}{d}\int T dy$$

gives:

$$\rho c V_z d \frac{\partial \overline{T}}{\partial z} = kd\left(\frac{\partial^2 \overline{T}}{\partial x^2} + \frac{\partial^2 \overline{T}}{\partial z^2}\right) + k\int_{y=0}^{y=d} \frac{\partial^2 T}{\partial y^2} dy + \dot{q}(x, y, z)d \quad (4)$$

$$k\int_{y=0}^{y=d} \frac{\partial^2 T}{\partial y^2} dy = k\frac{\partial T}{\partial y}\bigg|_{y=d} - k\frac{\partial T}{\partial y}\bigg|_{y=0} = -q''_{y=d} + q''_{y=0} \quad (5)$$

Experimental results show that $q''_{y=0} \gg q''_{y=d}$, hence the loss on the PDMS side can be negligible. Next, integrating in x-direction, from x=0 to x=w, gives the following:

$$w\rho c V_z d \frac{\partial \overline{T}}{\partial z} = \quad (6)$$

$$kwd\frac{\partial^2 \overline{T}}{\partial z^2} + kd\int_{x=0}^{x=w} \frac{\partial^2 T}{\partial x^2} dx + \int_{x=0}^{x=w} q''_{y=0}(x, z)dx + d\int_{x=0}^{x=w} \dot{q}(z)dx$$

The heat transfer in x-direction at the boundary is adiabatic, so:

$$k\int_{x=0}^{x=w} \frac{\partial^2 T}{\partial x^2} dx = k\frac{\partial T}{\partial x}\bigg|_{x=w} - k\frac{\partial T}{\partial x}\bigg|_{x=0} = 0 \quad (7)$$

$$wd\rho c V_z \frac{\partial \overline{T}}{\partial z} = kwd\frac{\partial^2 \overline{T}}{\partial z^2} + \int_{x=0}^{x=w} q''_{y=0}(x, z)dx + d\int_{x=0}^{x=w} \dot{q}(z)dx \quad (8)$$

$$d\int_{x=0}^{x=w} \dot{q}(z)dx = wd\rho c V_z \frac{\partial \overline{T}}{\partial z} - kwd\frac{\partial^2 \overline{T}}{\partial z^2} - \int_{x=0}^{x=w} q''_{y=0}(x, z)dx \quad (9)$$

where $\dot{q}(z)$ is the local heat source due to the chemical reaction averaged over channel width x and depth y. Here, temperature T is also averaged over the channel width x. $q''_{y=0}$ represents the heat flux coming from the chip surface and can be approximated by:

$$q''_{y=0} = H(x,z)[\overline{T}_{chip} - \overline{T}(z)] \quad (10)$$

wherein H(x,z) is the experimentally determined calibration heat loss coefficient for the system. Along the flow direction, between the locations $z_1$ and $z_2$, the total heat source can be obtained by integrating local heat source along z-direction. Setting $\overline{T} = T$ and rearranging gives the following equation:

$$d\int_{z_1}^{z_2}\int_{x=0}^{x=w} \dot{q}(z)dxdz = wd\rho c V_z[T(z_2) - T(z_1)] - \quad (11)$$

$$wd\left[k\frac{\partial T}{\partial z}\bigg|_{z_2} - k\frac{\partial T}{\partial z}\bigg|_{z_1}\right] - \int_{z_1}^{z_2}\int_{x=0}^{x=w} H(x,z)[T_{chip} - T(x,z)]dxdz$$

In this analytical approach, using the general form of energy equation, emphasis is kept on the heat source term and necessary simplifications have been done based on the previous numerical results. Equation 11 shows that enthalpy of reaction $$\left(\Delta H = \frac{\dot{q}}{n_{AB}}\right)$$

can be extracted based on temperature measurements of the flow field for this experimental configuration. From the enthalpy of reaction and the temperature, one can calculate further calorimetric measurements, such as the binding constant of the reaction, Gibbs free energy, change in free energy, entropy, and change in entropy from the temperature.

For example, the binding constant $K_D$ can be obtained by using the temperature profiles in energy balances using volumes bounded by $x_1$, $x_2$, $z_1$, $z_2$ and the channel height to determine the heat source $\dot{q}$ due to reaction in that volume. Repeating this calculation for several volumes, $x_2$, $x_3$, $z_1$, $z_2$; $x_3$, $x_4$, $z_1$, $z_2$ ... $x_n$, $x_{n+1}$, $z_1$, $z_2$, will provide information on the energy released for different amounts of the reactant and products. The measured heat source due to the reaction in each volume is related to the enthalpy of reaction and the binding constant. This information is used in a combined mass balance and binding constant definition, below, to iteratively determine the binding constant using the measured heat source due to the reaction in the different volumes:

$$(n_{ML})^2 - [N_i\Delta n_L + n_{MTOT} + K_D] + (N_i\Delta n_L)n_{MTOT} = 0$$

Figure 10A:
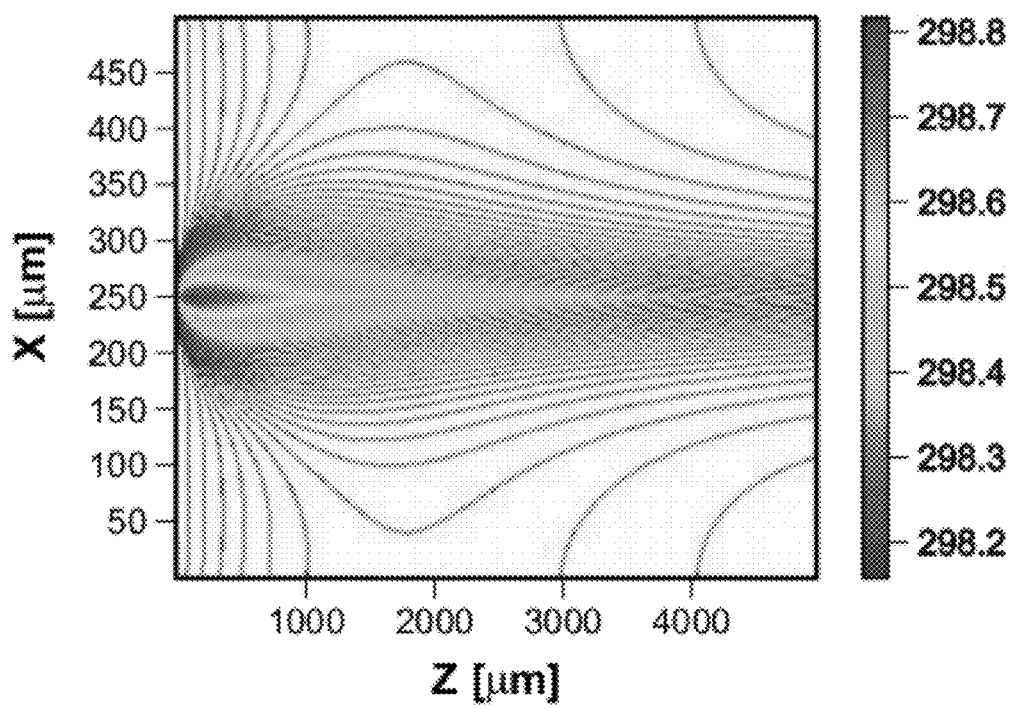
FIG. 10 depicts a simulated heat map (10a) and an experimental heat map (10b) of a reaction in a laminar flow channel, according to an illustrative embodiment of the invention.

In order to obtain accurate enthalpic measurements, the nanohole arrays should provide adequate measurement resolution while not interfering with neighboring sensors. To determine optimal nanosensor array placement, reaction simulations with nanoholes arrays in various configurations were performed. First, a model of a laminar flow channel with the dimensions mentioned with respect to FIG. 5 (w=500 µm, l=5000 μm) and depth equal to 10 μm was created in FLUENT, a computational fluid dynamics software. The continuity, Navier-Stokes, mass transport, and reaction rate equations were solved at 500,000 nodes for a steady state case of a NaOH+HCl reaction in 3D space to obtain a temperature field at the surface of the metal foil, shown in FIG. 10*a*. The model assumes a no slip condition at the walls of the channel and that the side walls are adiabatic. The thermophysical properties of the fluid mixture modeled as the properties of water at 298.15 K, as the temperature change of the reaction is only ±5 K and the mixture is mostly water. FIG. 10*a* depicts the heat map produced by this model, which is compared to an experimental result for a similar reaction shown in FIG. 10*b*.

Figure 10B:
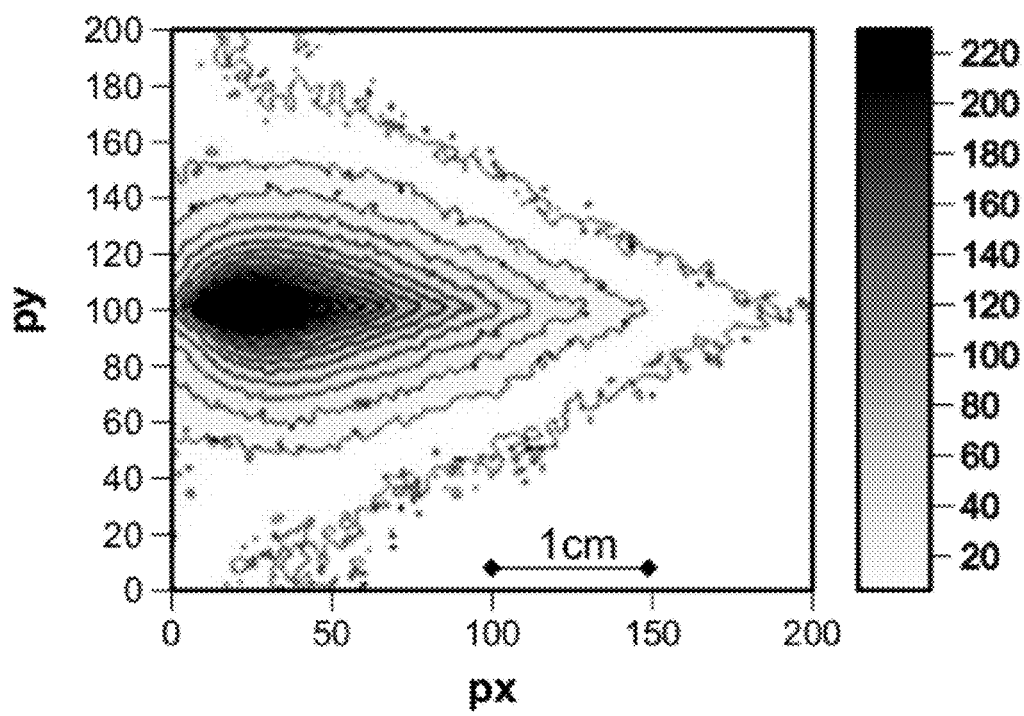

FIG. 10*b* depicts experimental results of a reaction between 0.25M NaOH and 0.25M HCl solutions in water in laminar flow measured with an infrared camera (Pradere et al., 2006). The solutions are configured in laminar flow with flow rate 1000 μl/h over a channel length of 40 mm. FIG. 10*a* is a heat simulation result of the same reagents in laminar flow with a flow rate of 90 μl/h over a channel length of 5 mm, which as shown in FIG. 10*a* give qualitatively similar temperature contours to the experimental heat map FIG. 10*b*. The simulated diffusion characteristics of the reaction zone, which is the tear drop shaped region, are also similar to the experimental diffusion characteristics. The similarities between the simulated and experimental results validate the FLUENT model.

Thermal boundary analysis was performed on the simulated model to analyze the temperature in the y-direction. The temperature sensed over the immediate vicinity of the metal foil was found to be 99.8610% of the average temperature normal to the channel. Since SPR sensors such as nanohole arrays only sense temperature in the near field, a thickness of λ/4 of the incident wavelength (~150 nm), this validates that near field sensing accurately represents the temperature of the entire channel.

A valid model for a temperature field of a reaction in a laminar flow channel also allows one to determine optimal nanohole array spacing. For the sensor spacing analysis, temperature, heat flux, and concentration at the metal foil surface (y=0 surface) are taken from the FLUENT model. Each term from Equation 11 is estimated at equally spaced points for multiple spacing values and the enthalpy of formation at each array may be estimated using the following equation:

$$\Delta H_{formation} = \frac{d \int_{z_1}^{z_2} \int_{x=0}^{x=w} \dot{q}(z) dx dz}{\frac{(\dot{m}_{NaCl}^{outlet} - \dot{m}_{NaCl}^{inlet})}{M_{NaCl}}} \quad (12)$$

So, enthalpy of formation is estimated using various array spacing algorithms and the map of the heat loss coefficient known by the simulation. The success of each spacing algorithm is determined by the accuracy of the estimated enthalpy of formation. Estimates of other known measurements, such as mass fraction and entropy, may be used alternatively or in addition to the enthalpy of formation. The procedure is repeated for different values of horizontal spacing between arrays, different inlet velocities, and different intervals in the z direction. The procedure may also be repeated for different array arrangements, diffusion rates, or other variables.

Three sensor spacing algorithms were investigated:

1. Taking the wall at x=0 as reference and placing sensors equally spaced with the sensor spacing distance;

2. Taking the center of the channel with respect to x as the reference, placing sensors equally spaced with the sensor spacing distance;

3. Taking the center of the channel with respect to x as the reference, but the first sensor will be half of the sensor spacing value away from the center (i.e. no sensor in the center).

Additionally, spacing for flow velocities of 0.0005 m/s, 0.005 m/s, and 0.05 m/s were investigated. As expected, for a channel of a given length, a larger resolution in the x-direction is required for higher flow rates since the diffusion width the x-direction is small due to the low residence time. As different reactions will have different diffusivities, the flow rate of the reagents can be varied to achieve the necessary resolution with respect to a set nanohole array spacing.

Figure 11:
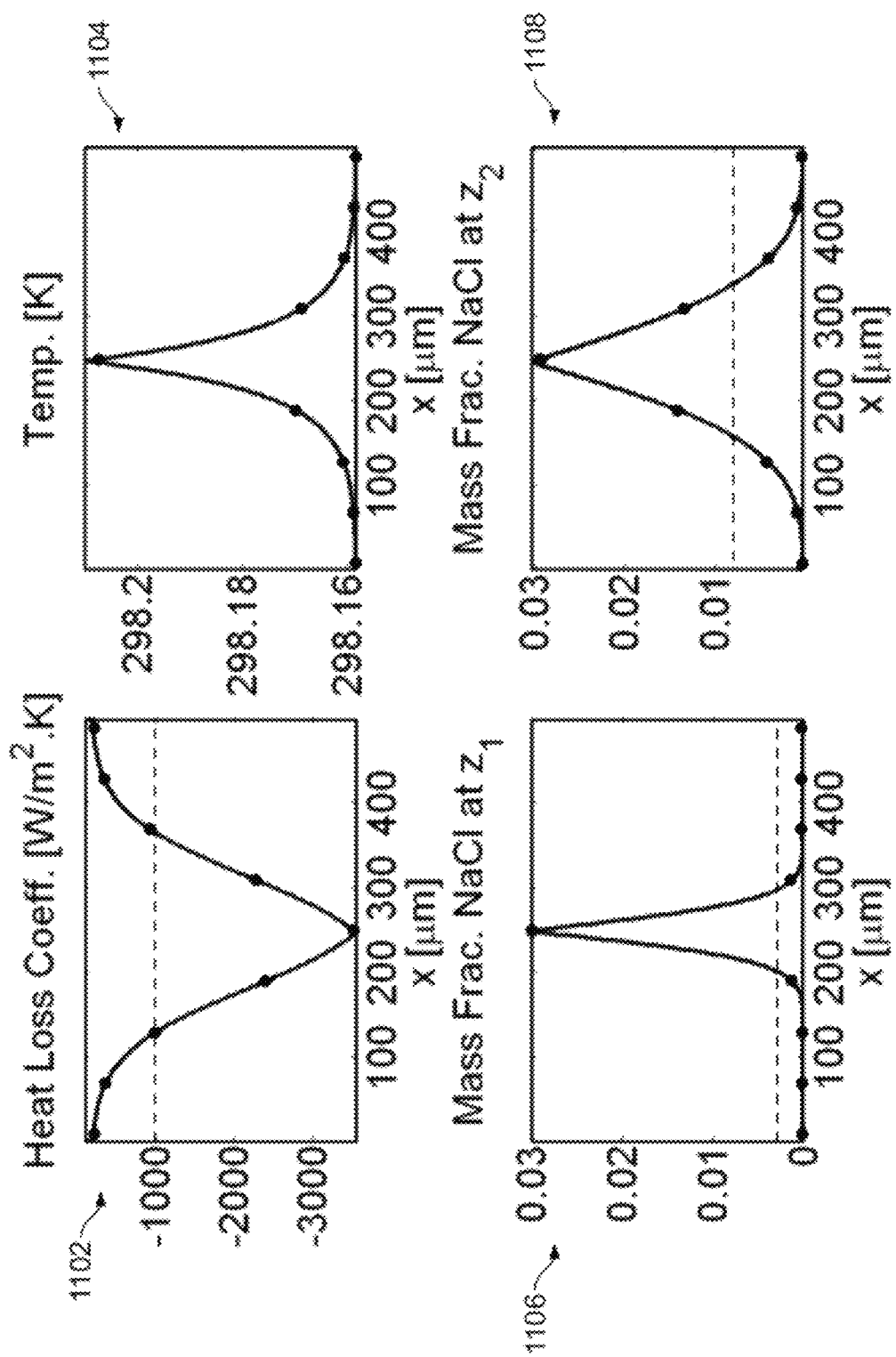
FIG. 11 depicts graphs illustrating simulation results for heat loss coefficient, temperature, and mass fractions at specific positions across the width of a laminar flow channel, according to an illustrative embodiment of the invention.

For sensor spacings ranging from 2 μm to 120 μm spaced with each of the aforementioned spacing algorithms, percent error starts deviating after 40 μm due to the shapes of the concentration, temperature, and heat loss coefficient curves as functions of x, which are similar to a Gaussian distribution. FIG. 11 depicts the heat loss coefficient 1102 and temperature 1104 curves versus x at z=50 μm for a flow rate of 0.0005 m/s. The mass fraction curves 1106 and 1108 of NaCl at $z_1$=50 μm (z1) and $z_2$=800 μm, respectively, are below curves 1102 and 1104. A 60 μm spacing configuration can adequately represent the heat loss and temperature averages across the width of the channel, but not the mass fraction at the regions near the inlet. This behavior is due to the low values of mass diffusivity coefficient in the x direction compared to the larger values of thermal conductivity (diffusivity) constant. At certain spacing configurations, sensor locations can correspond to locations where a single point can represent the total average of the curve (the vicinity of the horizontal lines in mass fraction graphs in FIG. 11). However, these locations are dependent on the curve characteristics and can change with many parameters such as the nature of reaction, and z-location. Therefore, the error analysis should be done with extra caution. The results show that this behavior starts to occur after 40 μm. Therefore, in an exemplary embodiment sensors are arranged in a grid with spacing of 10 to 30 μm.

This type of modeling can be used to determine optimal sensor spacing for other flow rates. In general, higher flow rates require more closely spaced sensors in the x direction, across the width of the channel. Furthermore, the model shown can be used to examine other algorithms of spacing sensors, such as spacing wherein sensors are more concentrated toward the middle of the channel. FLUENT or another computational fluid dynamics software may be used for the modeling.

Drug Development Application

Figure 12:
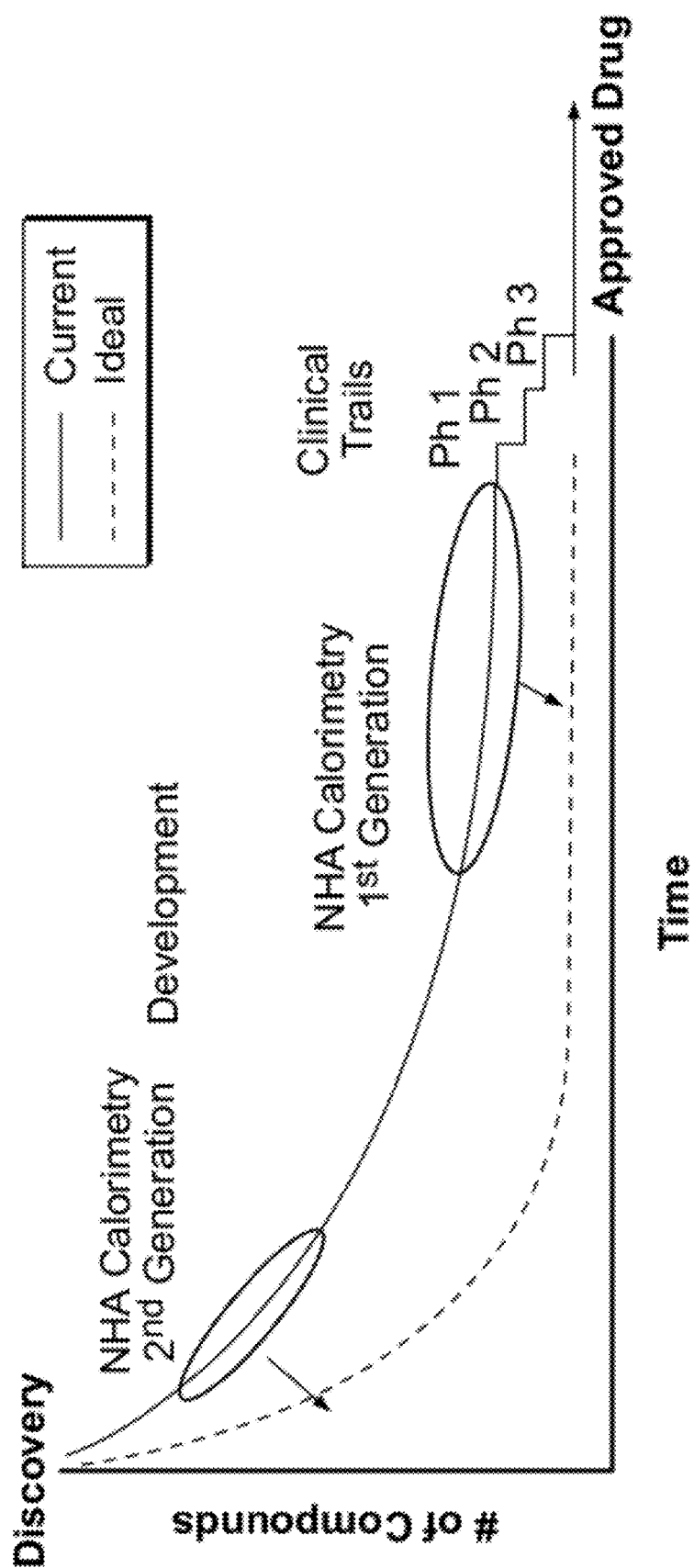
FIG. 12 is a graph illustrating the trend between the number of compounds versus time in a pharmaceutical research and development process.

FIG. 12 is a graph illustrating the trend between the number of compounds versus time in a pharmaceutical research and development process. Initially, there are a large number of compounds being investigated for a particular therapeutic target. Currently, high throughput screening is used at the start of the process, and calorimetry is generally not performed on the compounds until fairly late in the development process. One objective of the microfluidic calorimetry apparatus disclosed herein is to enable sensitive, fast, low volume calorimetry measurements so that calorimetry may be utilized earlier in the drug development, pushing the curve of number of compounds vs. time to the lower dotted line.

Figure 13:
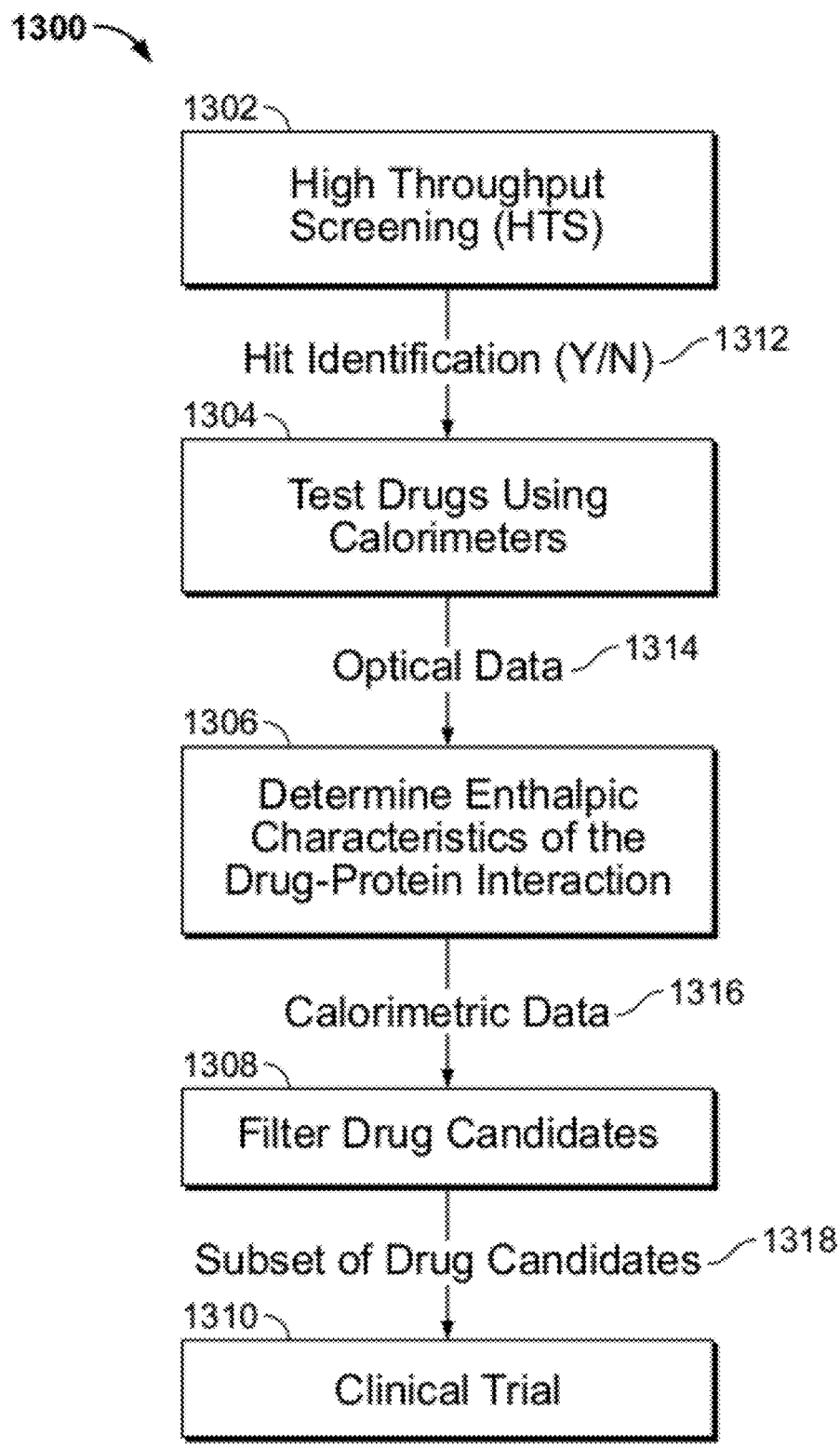
FIG. 13 is a flowchart for a method of pharmaceutical research and development utilizing the microfluidic calorimetry system of FIG. 1, according to an illustrative embodiment of the invention.

FIG. 13 is a flowchart for a method of pharmaceutical research and development. First, a high-throughput screening (HTS) is performed (step 1302). HTS is an automated method for determining if a biological entity, such as a protein, cells, an embryo, etc., reacts with a compound. Current HTS systems can test up to 100,000 compounds per day, and advances in HTS screening are continually increasing their output. While HTS allows a great number of compounds to be tested, it only gives a binary result for whether a compound is active or not. Other screening methods that are practical to perform on a large number of compounds may also or alternatively be used.

After high-throughput screening and/or other screening tests, compounds are next tested using calorimetry (step 1304). Compounds that reacted in a high throughput screening are currently tested using two calorimetry techniques: differential scanning calorimetry and isothermal scanning calorimetry. The inventive microfluidic calorimetry method disclosed herein can replace both differential scanning calorimetry and isothermal scanning calorimetry with faster results and potentially using as little as one-one thousandth the reagent consumption of current calorimeters. As discussed above with respect to FIG. 9, the optical data 1314 is processed to determine enthalpic characteristics of the drug-protein interaction (1306), producing calorimetric data 1316. This data is then analyzed to filter drug candidates (1308). The filtering may return all compounds with enthalpies and/or entropies in a certain range. The filtering may alternatively select a given number of compounds with best results. The calorimetric measurements may be weighted and summed to give each compound a composite score. The result of the filtering is a subset of drug candidates 1318 that are selected for a first round of a clinical trial after an institutional board review. Other pre-clinical studies, such as in vivo or in vitro experiments, may be required before a clinical study.

While preferable embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

REFERENCES

Krishnan, A. et al. "Evanescently coupled resonance in surface plasmon enhanced transmission," *Optics Communications*, Vol. 200, pp. 1-7, 2001.
Ji, J. et al. "High-throughput nanohole array based system to monitor multiple binding events in real time," *Analytical Chemistry*, Vol. 80, pp. 2491-2498, 2008.
Leach, A. et al. "Flow injection analysis in a microfluidic format," *Analytical Chemistry*, Vol. 75, No. 5, pp. 967-972, 2003.
Lindquist, N. et al. "Sub-micron resolution surface plasmon resonance imaging enabled by nanohole arrays with surrounding Bragg mirrors for enhanced sensitivity and isolation," *Lab on a Chip*, Vol. 9, pp. 382-387, 2009.
Pradere, C. et al. "Processing of temperature field in chemical microreactors with infrared thermography," *QIRT*, Vol. 3, No. 1, pp. 117-135, 2006.

What is claimed is:

1. A method for calorimetry comprising:
providing a calorimetry apparatus comprising:
a microfluidic laminar flow channel;
two inlets in fluid connection with the microfluidic laminar flow channel, the inlets allowing fluid to flow into the microfluidic laminar flow channel; and
a plurality of microscale temperature sensors disposed below the microfluidic laminar flow channel at known positions relative to boundaries of the microfluidic laminar flow channel;
continuously flowing fluids from each of the two inlets into the microfluidic laminar flow channel such that a chemical reaction occurs at least at a diffusion interface of the fluids, wherein a ratio of fluid from a first one of the inlets to fluid from a second one of the inlets varies across the diffusion interface;
receiving data output from each of the plurality of microscale temperature sensors;
obtaining a local temperature at each of the respective positions of the plurality of microscale temperature sensors based on the data output from each of the plurality of microscale temperature sensors;
processing the data output from each of the plurality of microscale temperature sensors to determine a temperature change at each of the known positions along the microfluidic laminar flow channel;
calculating a first calorimetry measurement indicative of energetics associated with the chemical reaction at a first location where the ratio of the fluid from the first inlet to the fluid from the second inlet has a first value based on the temperature change at the respective position of at least a first one of the microscale temperature sensors in the microfluidic laminar flow channel;
calculating a second calorimetry measurement indicative of energy associated with the chemical reaction at a second location, different from the first location, where the ratio of the fluid from the first inlet to the fluid from the second inlet has a second value, different from the first value, based on the temperature change at the respective position of at least a second one of the microscale temperature sensors in the microfluidic laminar flow channel.

2. The method of claim 1, wherein the temperature sensors comprise:
a plurality of aperture arrays in a metal layer disposed below the laminar flow channel; and
at least one optical sensor for measuring light transmitted through the plurality of aperture arrays.

3. The method of claim 2, wherein calculating a calorimetry measurement comprises processing data related to the light measured from at least a subset of the plurality of aperture arrays and the respective positions of the aperture arrays in the channel.

4. The method of claim 2, wherein calculating a calorimetry measurement comprises processing data from the at least one optical sensor according the principles of plasmon mediated optical transmission.

5. The method of claim 2, wherein
data output by the at least one optical sensor depends on both a chemical concentration and a temperature;
the chemical concentration profile in the laminar flow channel is known; and
processing the data from the at least one optical sensor comprises recovering the temperature of the reaction by deconvolving the data with the chemical concentration.

6. The method of claim 2, wherein the local temperatures include local temperatures at multiple locations along a length of the flow channel and at multiple locations across the width of flow channel.

7. The method of claim 1, wherein calculating a calorimetry measurement further comprises calculating the enthalpy of formation according to the following equations:

$$d\int_{z_1}^{z_2}\int_{x=0}^{x=w} \dot{q}(z)dxdz = wd\rho c V_z[T(z_2) - T(z_1)] -$$

$$wd\left[k\frac{\partial T}{\partial z}\bigg|_{z_2} - k\frac{\partial T}{\partial z}\bigg|_{z_1}\right] - \int_{z_1}^{z_2}\int_{x=0}^{x=w} H(x,z)[T_{chip} - T(x,z)]dxdz;\ \text{and}$$

$$\Delta H_{formation} = \frac{d\int_{z_1}^{z_2}\int_{x=0}^{x=w}\dot{q}(z)dxdz}{\frac{(\dot{m}_{AB}^{outlet} - \dot{m}_{AB}^{inlet})}{M_{AB}}}$$

wherein the calculation is bounded by a volume defined by x1, x2, z1, z2 coordinates on the channel; and
wherein variables used in the equation are defined as follows:
d is channel depth;
q is heat source due to reaction;
w is channel width;
p is density of the fluid;
c is specific heat of the fluid;
$V_z$ $\Delta$ is velocity in z-direction;
T is temperature;
k is thermal conductivity of the solution;
H is heat loss calibration coefficient of the chip surface;
$\Delta H$ is enthalpy of formation of the complex AB;
ṁ is mass flux in the channel; and
M is molecular weight of the complex.

8. The method of claim 1, wherein calculating a calorimetry measurement comprises calculating at least one of enthalpy of the reaction, a binding constant of the reaction, Gibbs free energy, change in free energy, entropy, and change in entropy.

9. The method of claim 1, further comprising selecting the flow rate of at least one of the two fluids based on the diffusivity of the fluids.

10. The method of claim 1, further comprising disposing at least one reagent of the chemical reaction in a solution so that the enthalpy associated with the chemical reaction causes a temperature change in the solution.

11. The method of claim 1, further comprising:
sensing an environmental system temperature; and
controlling the environmental system temperature by receiving the environmental system temperature from a temperature sensor and heating or cooling the calorimetry apparatus with a temperature controller as necessary to maintain a nearly constant environmental system temperature.

12. The method of claim 1, wherein fluid traveling from the two inlets into the laminar flow channel diffuses in the laminar flow channel in a diffusion region that is stationary over time after an initialization period.

13. The method of claim 12, the method comprising measuring a baseline temperature of a fluid in a region outside of the diffusion region.

14. The method of claim 1, wherein flowing fluids further comprises introducing a reagent into a flow using an injection valve in connection with at least one of the inlets.

15. The method of claim 1, further comprising obtaining the local temperatures at the plurality of microscale temperature sensors.

16. The method of claim 1, wherein the ratio of the fluid from the first one of the inlets to the fluid from the second one of the inlets varies across a width of the microfluidic laminar flow channel, the method further comprising:
obtaining, for the first location at a first distance across the width of the microfluidic laminar flow channel, the first value for the ratio of the fluid from the first inlet to the fluid from the second inlet at the first location; and
obtaining, for the second location at a second distance across the width of the microfluidic laminar flow channel, the second value for the ratio of the fluid from the first inlet to the fluid from the second inlet at the second location.

17. A method for determining a calorimetry value for a reaction comprising:
receiving optical sensor data from each of a plurality of optical sensors positioned under apertures at known positions along a microfluidic channel while two reagents are being continuously flowed through the microfluidic channel and reacting at least at their diffusion interface, wherein a ratio of the two reagents varies across the diffusion interface;
processing at least a subset of the received optical data to determine a temperature change at each of the known positions along the microfluidic channel;
calculating a first calorimetry value indicative of the energetics associated with the chemical reaction at a first location where the ratio of the two reagents has a first value based at least on the temperature change at a the respective position of at least a first one of the plurality of the optical sensors and a flow rate of the reagents; and
calculating a second calorimetry value indicative of energetics associated with the chemical reaction at a second location, different from the first location, where the ratio of the two reagents has a second value, different from the first value, based at least on the temperature change at a the respective position of at least a second one of the plurality of the optical sensors and a flow rate of the reagents.

18. The method of claim 17, further comprising disposing at least one reagent of the at least one chemical reaction in a solution so that the enthalpy associated with the at least one chemical reaction causes a detectable temperature change in the solution.

19. The method of claim 17 further comprising:
sensing an environmental system temperature; and
controlling the environmental system temperature by receiving the environmental system temperature from a temperature sensor and heating or cooling the system with a temperature controller as necessary to maintain a nearly constant environmental system temperature.

20. The method of claim 19, further comprising setting the environmental system temperature as a reference temperature used for processing the received optical data.

21. The method of claim 17, wherein data from the at least one optical sensor is processed according the principles of plasmon mediated optical transmission.

22. The method of claim 17, wherein
the data related to the detected light depends on both a chemical concentration and a
temperature;
the chemical concentration profile in the laminar flow channel is known; and
processing the data related to the detected light comprises recovering the temperature of the reaction by deconvolving the data with the chemical concentration.

23. The method of claim 22, wherein the calorimetry value is one of a binding constant of the reaction, Gibbs free energy, change in free energy, entropy, and change in entropy from the temperature.

24. The method of claim 17, wherein
the received optical data comprises at least one measurement from at least one aperture array positioned outside of a region where the reagents are reacting; and
processing the data comprises using the at least one measurement from the at least one aperture array outside of the region where the reagents are reacting as a baseline temperature of at least one reagent.

25. The method of claim 17, wherein processing the received optical data further comprises integrating the optical data over time.

26. The method of claim 17, wherein the ratio of the two reagents varies across a width of the microfluidic laminar flow channel, the method further comprising:
obtaining, for the first location at a first distance across the width of the microfluidic laminar flow channel, the first value for the ratio of the two reagents at the first location; and
obtaining, for the second location at a second distance across the width of the microfluidic laminar flow channel, the second value for the ratio of the two reagents at the first location.

27. A method for pharmaceutical development comprising:
generating optical sensor data on a plurality of reactions between a protein and each of a plurality of drugs using at least one calorimetry apparatus comprising:
a microfluidic laminar flow channel;
at least two inlets in fluid connection with the microfluidic laminar flow channel, the inlets allowing fluid to flow into the microfluidic laminar flow channel wherein a ratio of fluid from a first one of the inlets to fluid from a second one of the inlets varies across a diffusion interface of the fluids; and
a plurality of microscale temperature sensors disposed below the microfluidic laminar flow channel at known positions relative to boundaries of the microfluidic laminar flow channel;
receiving data output from each of the plurality of microscale temperature sensors;
obtaining a local temperature at each of the respective positions of the plurality of microscale temperature sensors based on the data output from each of the plurality of microscale temperature sensors;
processing the data output from each of the plurality of microscale temperature sensors to determine a temperature change at each of the known positions along the microfluidic laminar flow channel;
determining, for each of the plurality of reactions, a first calorimetry measurement of the reaction at a first location where the ratio of the fluid from the first inlet to the fluid from the second inlet has a first value based on the temperature change at the respective position of at least a first one of the sensors in the microfluidic laminar flow channel;
determining, for each of the plurality of reactions, a second calorimetry measurement of the reaction at a second location, different from the first location, where the ratio of the fluid from the first inlet to the fluid from the second inlet has a second value, different from the first value, based on the temperature change at the respective position of at least a second one of the sensors in the microfluidic laminar flow channel; and
selecting based on the at least one calorimetry measurement one of the plurality of drugs for further clinical investigation.

28. The method of claim 27, wherein the ratio of the fluid from the first one of the inlets to the fluid from the second one of the inlets varies across a width of the microfluidic laminar flow channel, the method further comprising:
obtaining, for the first location at a first distance across the width of the microfluidic laminar flow channel, the first value for the ratio of the fluid from the first inlet to the fluid from the second inlet at the first location; and
obtaining, for the second location at a second distance across the width of the microfluidic laminar flow channel, the second value for the ratio of the fluid from the first inlet to the fluid from the second inlet at the second location.

29. The method of claim 27, further comprising obtaining the local temperatures at the plurality of microscale temperature sensors.

30. The method of claim 29, wherein the wherein the local temperatures include local temperatures at multiple locations along a length of the flow channel and at multiple locations across the width of flow channel.

* * * * *